United States Patent
Mukherjee et al.

(10) Patent No.: US 11,679,103 B2
(45) Date of Patent: Jun. 20, 2023

(54) MULTI-TARGETING AGENTS FOR ALZHEIMER'S DISEASE THERAPY

(71) Applicant: The Regents of the University of California, Oakland, CA (US)

(72) Inventors: Jogeshwar Mukherjee, Irvine, CA (US); Aparna Baranwal, Cerritos, CA (US); Heather Ho, Irvine, CA (US); Gurleen Samra, Reseda, CA (US); Kenneth Dang, San Francisco, CA (US); Megan Rose Felix, Oakley, CA (US)

(73) Assignee: The Regents of the University of California, Oakland, CA (US)

( * ) Notice: Subject to any disclaimer, the term of this patent is extended or adjusted under 35 U.S.C. 154(b) by 567 days.

(21) Appl. No.: 16/698,949

(22) Filed: Nov. 27, 2019

(65) Prior Publication Data

US 2020/0171016 A1    Jun. 4, 2020

Related U.S. Application Data

(60) Provisional application No. 62/774,105, filed on Nov. 30, 2018.

(51) Int. Cl.
| | |
|---|---|
| A61K 31/4439 | (2006.01) |
| A61K 47/54 | (2017.01) |
| A61P 25/28 | (2006.01) |
| A61K 31/277 | (2006.01) |
| A61K 31/445 | (2006.01) |

(52) U.S. Cl.
CPC ........ *A61K 31/4439* (2013.01); *A61K 31/277* (2013.01); *A61K 31/445* (2013.01); *A61K 47/545* (2017.08); *A61P 25/28* (2018.01)

(58) Field of Classification Search
CPC combination set(s) only.
See application file for complete search history.

(56) References Cited

PUBLICATIONS

Samra (Dual targeting agents for Aβ plaque/P-glycoprotein and Aβ plaque/nicotinic acetylcholine α4β2* receptors—potential approaches to facilitate Aβ plaque removal in Alzheimer's disease brain, Medicinal Chemistry Research (2018) 27:1634-164, Apr. 7, 2018).*
Aller et al., "Structure of P-glycoprotein reveals a molecular basis for poly-specific drug binding." Science 323:1718-1722 (2009).
Ariza et al., "Tau positron emission tomography (PET) imaging: past, present, and future." J Med Chem 58:4365-4382 (2015).
Bacyinski et al., "The paravascular pathway for brain waste clearance: current understanding, significance and controversy." Front Neuroanat 11:101 (2017).
Baranwal et al., "[18F]Fluorodeoxyglycosylamines: Maillard reaction of 18F-FDG with biological amines." J Label Compds Radiopharm 57:86-91 (2014).
Bartels, A., "Blood brain barrier P-glycoprotein function in neurodegenerative disease." Curr Pharm Des 17:2771-2777 (2011).
Barten et al., "Therapeutic strategies for Alzheimer's disease." Mol Neurobiol 37:171-186 (2008).
Braak et al., "Neuropathological staging of Alzheimer related changes." Acta Neuropathol 82:239-259 (1991).
Brendel et al., "Cross-sectional comparison of small animal [18F]florbetaben amyloid-PET between transgenic AD mouse models." PLoS ONE 10(2):e0116678 (2015).
Chattopadhyay et al., "Synthesis and evaluation of nicotine α4β2 receptor ligand, 5-(3'-fluoropropyl)-3-(2-(S)-pyrrolidinyl)methoxy)pyridine (18Fnifrolidine) in rodents and imaging by PET in non-human primate." J Nucl Med 46:130-140 (2005).
Coleman et al., "Brain and brown adipose tissue metabolism in Tg 2576 transgenic mice models of Alzheimer's disease assessed using 18F-FDG PET." Mol Imag 16:1-9 (2017).
Deane et al., "Clearance of amyloid-b peptide across the blood-brain barrier: Implications for therapies in Alzheimer's disease." CNS Neurol Disord Drug Targets 8:16-30 (2009).
Doody et al., "Phase 3 trials of solanezumab for mild-to-moderate Alzheimer's disease." N Engl J Med 370:311-321 (2014).
Filser et al., "Pharmacological inhibition of BACE1 impairs synaptic plasticity and cognitive functions." Biol Psych 77:729-739 (2015).
Garcia-Alloza et al., "Curcumin labels amyloid pathology in vivo, disrupts existing plaques, and partially restores distorted neurites in an Alzheimer's mouse model." J Neurochem 102:1095-1104 (2007).
Gerenu et al., "Curcumin/melatonin hybrid 5-(4-hydroxyphenyl)-3-oxo-pentanoic acid [2-(5-methoxy-1H-indol-3-yl)-ethyl]-amide ameliorates AD-like pathology in the APP/PS1 mouse mode." ACS Chem Neurosci 6:1393-1399 (2015).
Hu et al., "Clinical development of curcumin in neurodegenerative disease." Expert Rev Neurother 15:629-637 (2015).
Jessen et al., "The glymphatic system: a beginners guide." Neurochem Res 40:2583-2599 (2015).
Krishnamurthy et al., "A proposed role for efflux transporters in the pathogenesis of hydrocephalus." Croat Med J 55:66-76 (2014).
Leinenga et al., "Scanning ultrasound removes amyloid-beta and restores memory in an Alzheimer's disease mouse model." Sci Transl Med 7(278):278ra33 (2015).
Mancuso et al., "Pharmacological and toxicological aspects." Food Chem Toxicol 65:185-195 (2014).
Moghbel et al., "Amyloid-b imaging with PET in Alzheimer's disease: is it feasible with current radiotracers and technologies?" Eur J Nucl Mol Imag 39:202-208 (2012).
Mukherjee et al. "Human brain imaging of nicotinic acetylcholine α4β2* receptors using [18F]Nifene: selectivity, functional activity, toxicity, aging effects, gender effects and extrathalamic pathways." J Comp Neurol 526:80-96 (2018).

(Continued)

*Primary Examiner* — Kathrien A Hartsfield
(74) *Attorney, Agent, or Firm* — Gavrilovich, Dodd & Lindsey LLP

(57) ABSTRACT

The disclosure provides for multi-targeting agents that assist in the targeted removal of amyloid beta plaques from the brain and surrounding vasculature of subjects with Alzheimer's disease, and methods of treatment thereof.

19 Claims, 11 Drawing Sheets

(56) References Cited

PUBLICATIONS

Pahnke et al., "Clinicopathologic function of cerebral ABC transporters-implications for the pathogenesis of Alzheimers disease." Curr Alzheimers Res 5:396-405 (2008).
Pan et al., "Evaluation of [11C] TAZA for amyloid Aβ plaque imaging in postmortem Alzheimer's disease brain region and whole body distribution in rodent PET/CT." Synapse 70:163-176 (2016).
Pi et al., "Tacrine-6-ferulic acid, a novel multifunctional dimer, inhibits amyloid-β mediated Alzheimer's disease associated pathogenesis in vitro and in vivo." PLoS ONE 7:e31921 (2012).
Pichika et al., "Nicotine α4β2 receptor imaging agents. Part III. Synthesis and evaluation of 18F-Nifzetidine in rodents and imaging by PET in non-human primate." Nucl Med Biol 38:1183-1192 (2011).
Pichika et al., "Nicotine α4β2 receptor imaging agents. Part IV. Synthesis and evaluation of 18F-nifrolene in rodents and non-human primate by PET imaging." Nucl Med Biol 40:117-125 (2013).
Posadas et al., "Nicotinic receptors in neurodegeneration." Curr Neuropharmacol 11:298-314 (2013).
Qosa et al., "Enhanced brain amyloid beta clearance by rifamycin and caffeine as a possible protective mechanism against Alzheimers disease." J Alz Dis 31:151-156 (2012).
Ryu et al., "Curcumin and dehydrozingerone derivatives: synthesis, radiolabeling, and evaluation for β-amyloid plaque imaging." J Med Chem 49:6111-6119 (2006).
Salloway et al., "Two phase 3 trials of bapineuzumab in mild-to-moderate Alzheimers disease." N Engl J Med 370:322-333 (2014).
Samra et al., "Development of fluorescent probes for imaging α4β2* nicotinic acetylcholine receptors." Bioorg Med Chem Lett 28:371-377 (Feb. 1, 2018).
Samra et al., "Dual targeting agents for Aβ plaque/P-glycoprotein and Aβ plaque/nicotinic acetylcholine α4β2* receptors—potential approaches to facilitate Aβ plaque removal in Alzheimer's disease brain." Medicinal Chemistry Research 27:1634 1646 (Apr. 7, 2018).
Schenk et al., "Immunization with amyloid-beta attenuates Alzheimer's disease like pathology in the PDAPP mouse." Nature 402:537-540 (1999).
Sgarbossa et al., "Ferulic acid: a hope for Alzheimer's disease therapy from plants." Nutrients 7:5764-5782 (2015).
Siemers et al., "Phase 3 solanezumab trials: secondary outcomes in mild Alzheimer' disease patients." Alzheimers Dement 12:110-120 (2016).
Sultana et al., "Ferulic acid ethyl ester as a potential therapy in neurodegenerative disease." Biochim Biophys Acta 1822:748-752 (2012).
Syvanen et al., "Advances in PET imaging of Pglycoprotein function at the blood-brain barrier." ACS Chem Neurosci 4:225-237 (2013).
Tahara et al., "P-glycoprotein plays a major role in the efflux of fexofenadine in the small intestine and blood brain barrier, but only a limited role in its biliary excretion." Drug Metab Dis 33:963-968 (2005).
Tampellini et al., "Synaptic activity and Alzheimer's disease: a critical update." Front Neurosci 9:423 (2015).
Vassar et al., "BACE1 inhibitor drugs in clinical trials for Alzheimer's disease." Alzheimer's Res & Ther 6:89 (2014).
Venigalla et al., "Novel promising therapeutics against chronic inflammation and neurodegeneration in Alzheimer's disease." Neurochem Int 95:63-74 (2016).
Vlaming et al., "PET-CT imaging with [18F]-gefitinib to measure Abcd1a/1b (P-gp) and Abcg2 (Bcrp1) mediated drug—drug interactions at the murine blood-brain barrier." Nucl Med Biol 42:833-841 (2015).
Yan et al., "Protective effects of ferulic acid in amyloid precursor protein plus presenilin-1 transgenic mouse model of Alzheimer's disease." Biol Pharm Bull 36:140-143 (2013).
Zhao et al., "Fexofenadine brain exposure and the influence of blood brain barrier P-glycoprotein after fexofenadine and terfenadine administration." Drug Metab Disp 37:529-535 (2009).
Agatonovic-Kustrin et al. "A molecular approach in drug development for Alzheimer's disease." Biomed Pharmacother 106:553-565 (2018).
Braak et al., "Stages of the pathologic process in Alzheimer's disease age categories from 1 to 100 years." J Neuropathol Exp Neurol. 70:960-969 (2011).
Matsumura et al., "Phenyldiazenyl benzothiazole derivatives as probes for in vivo imaging of neurofibrillary tangles in Alzheimer's disease brains." Med Chem Commun. 2:596-600 (2011).
Stephenson et al. Fluoropegylated (FPEG) imaging agents targeting Ab aggregates. Bioconjug Chem. 18:238-246 (2007).
Weiner et al. "Impact of the Alzheimer's disease neuroimaging initiative 2004-2014." Alzheimers Dement. 11:865-884 (2014).

* cited by examiner

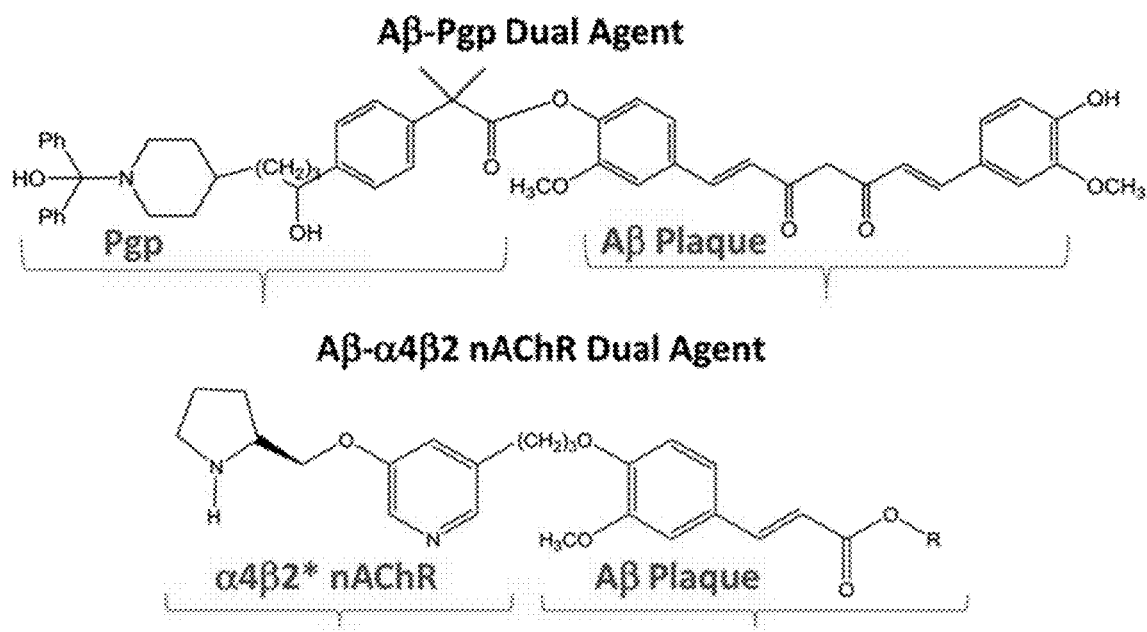
FIG. 1
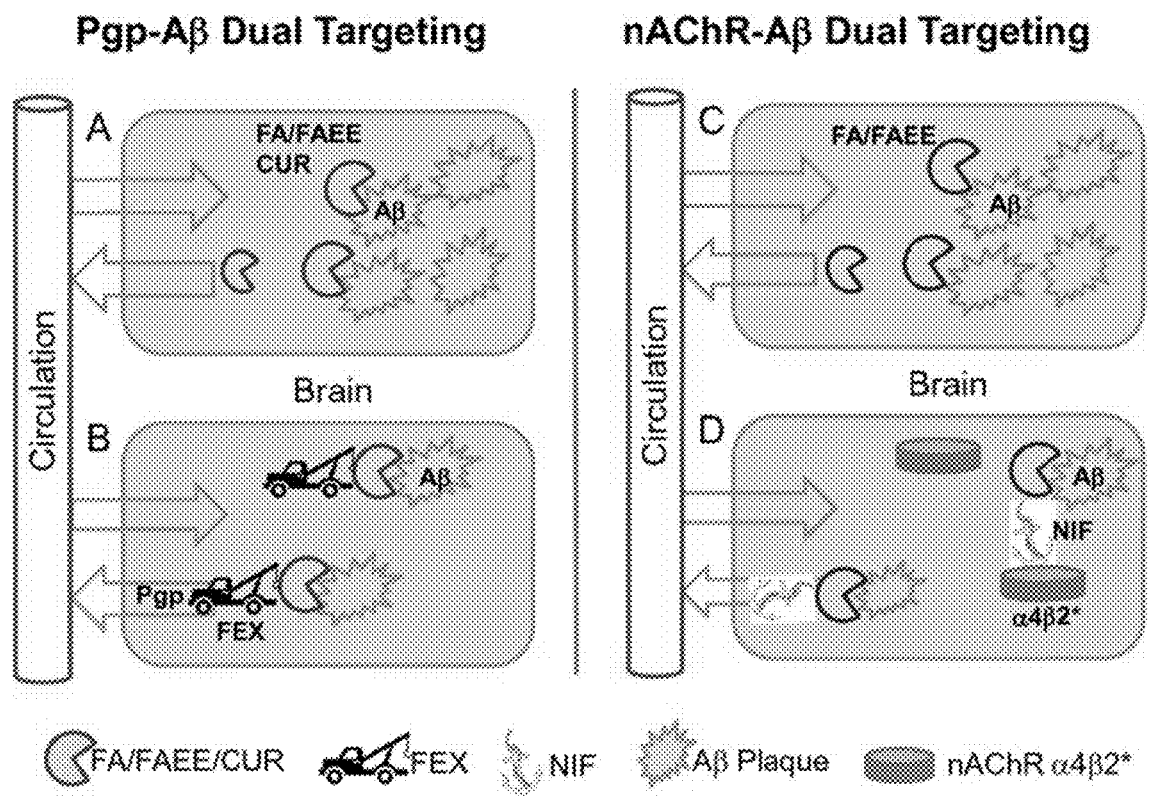
FIG. 2A-D

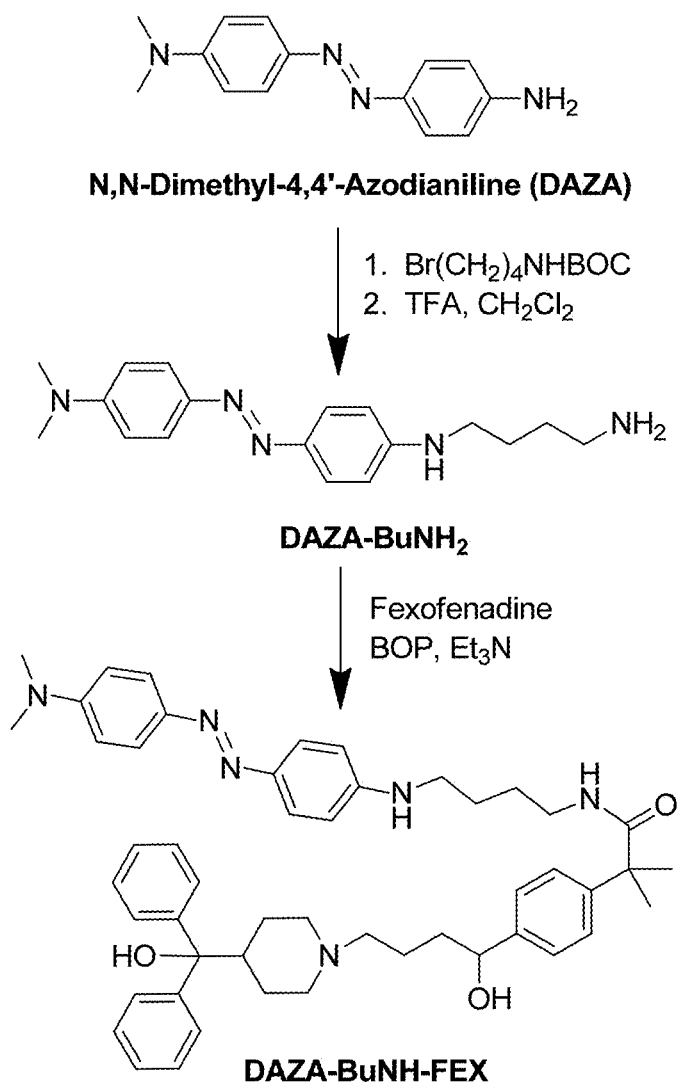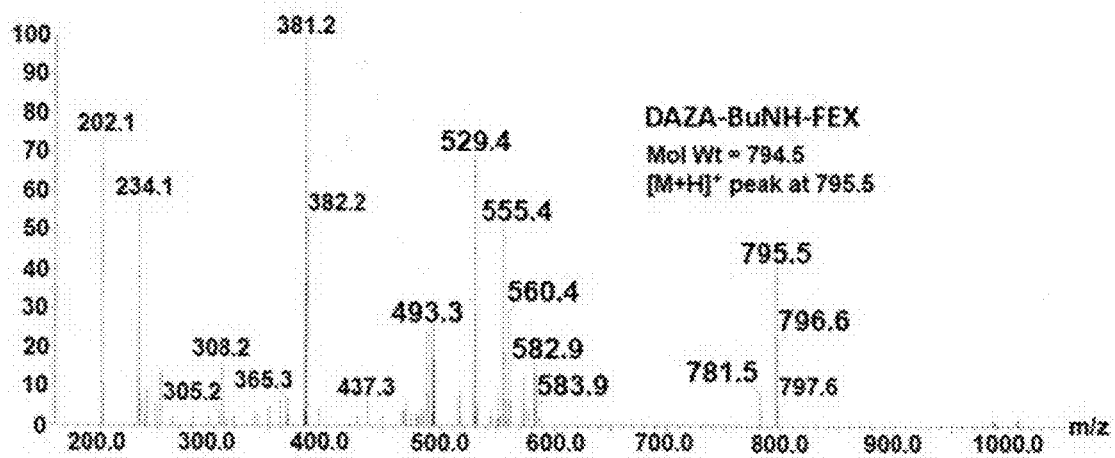
FIG. 7

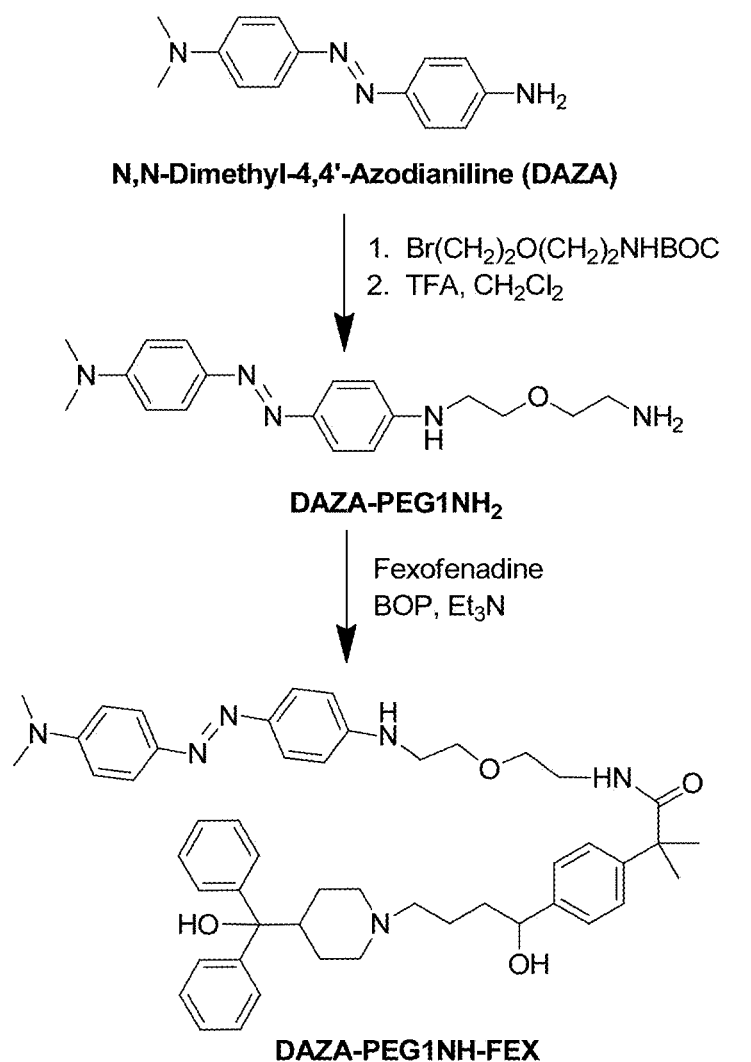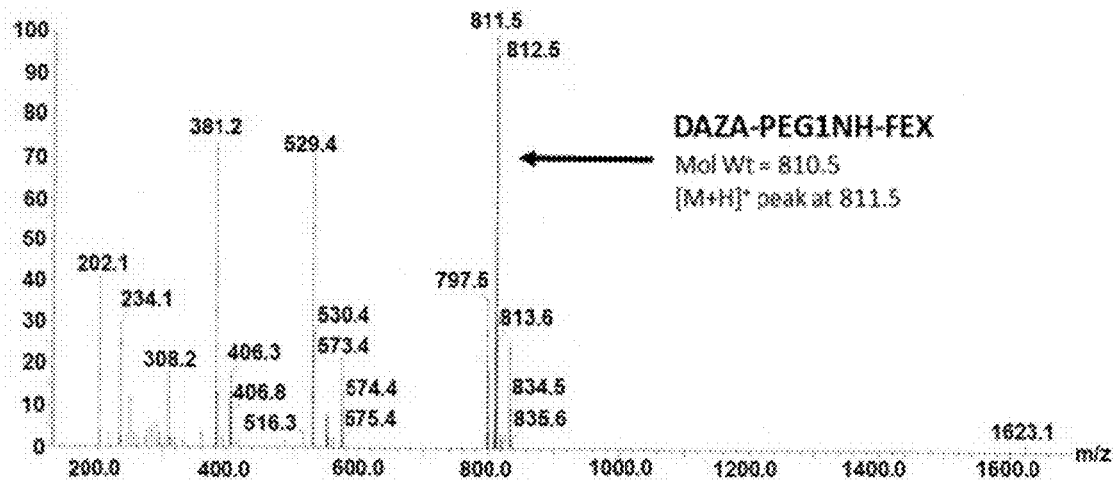
FIG. 8

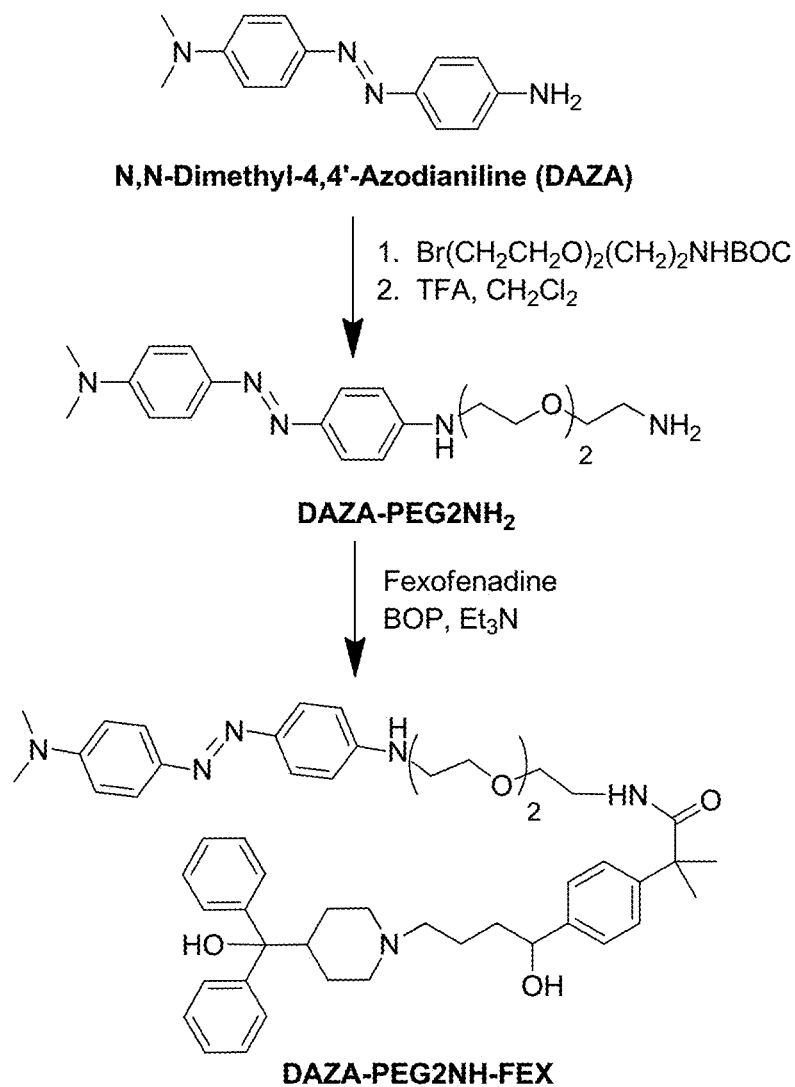
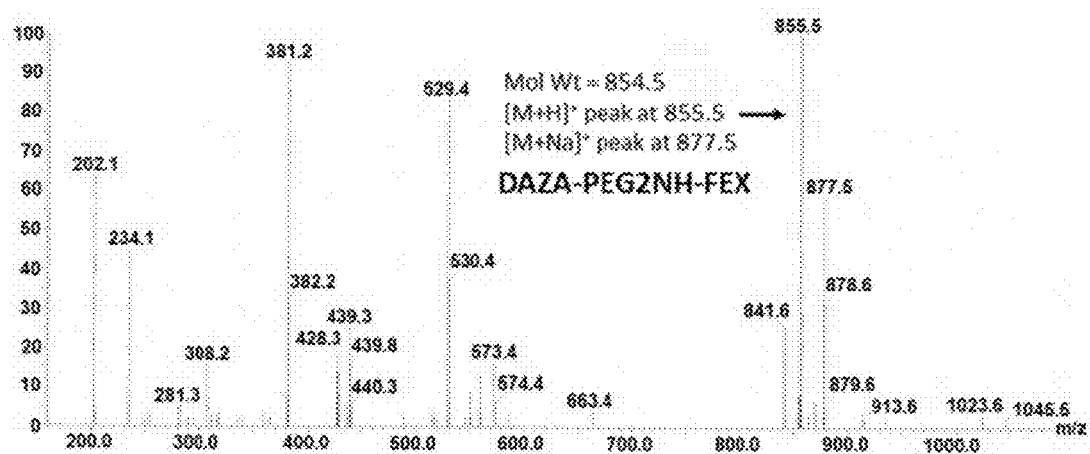
FIG. 9

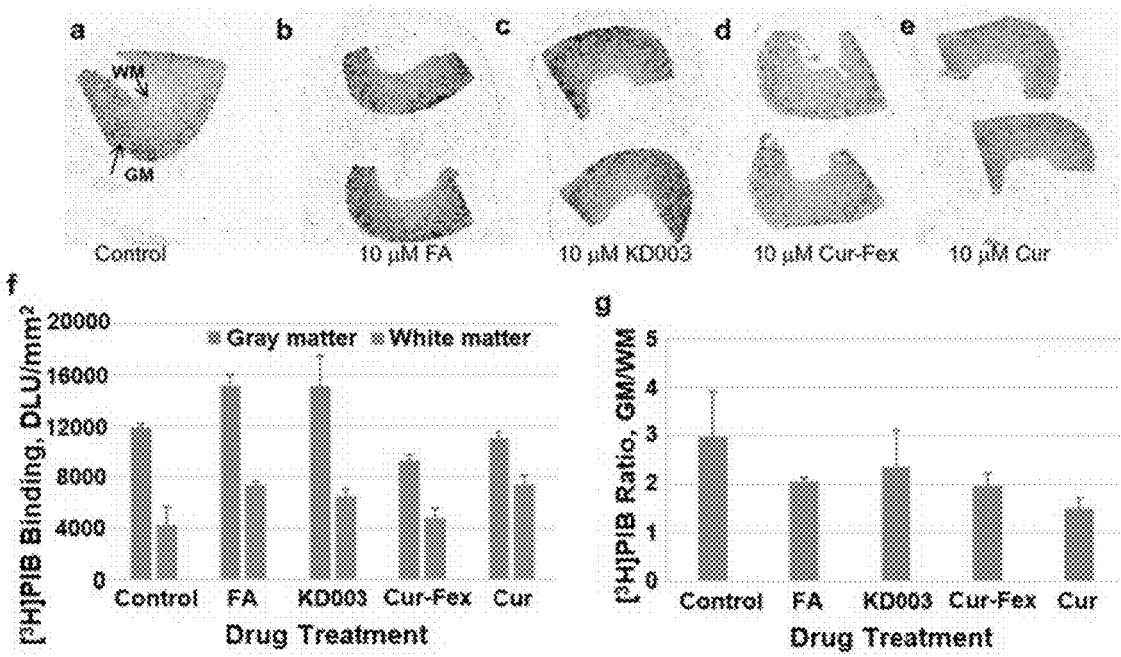
FIG. 10A-G
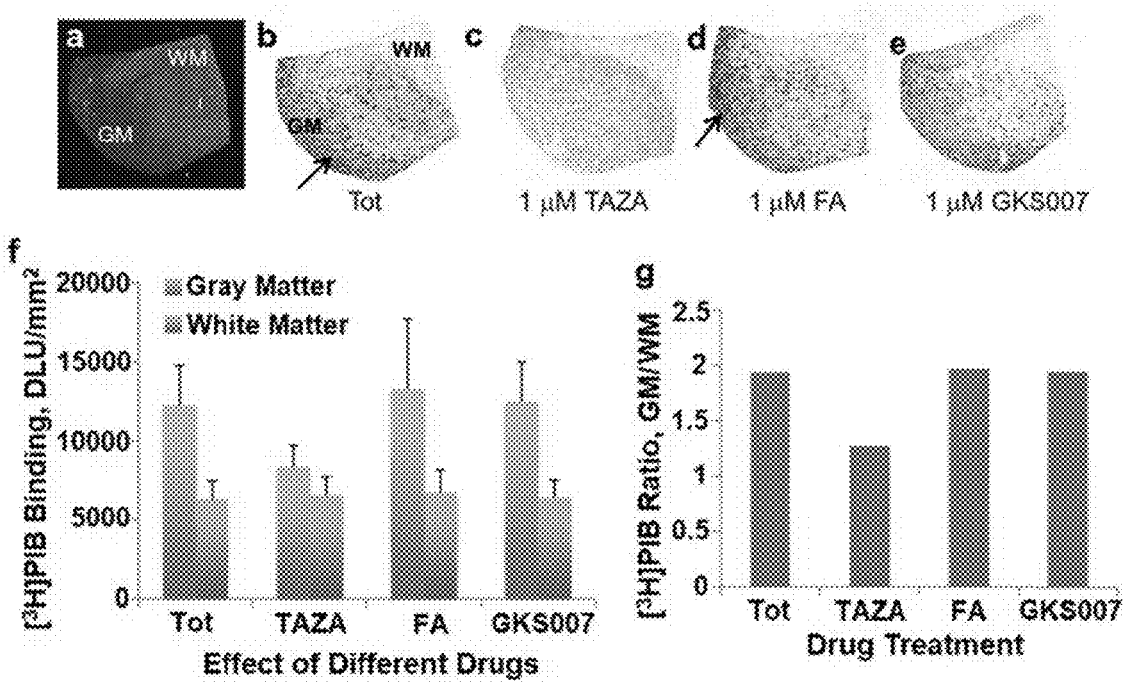
FIG. 11A-G

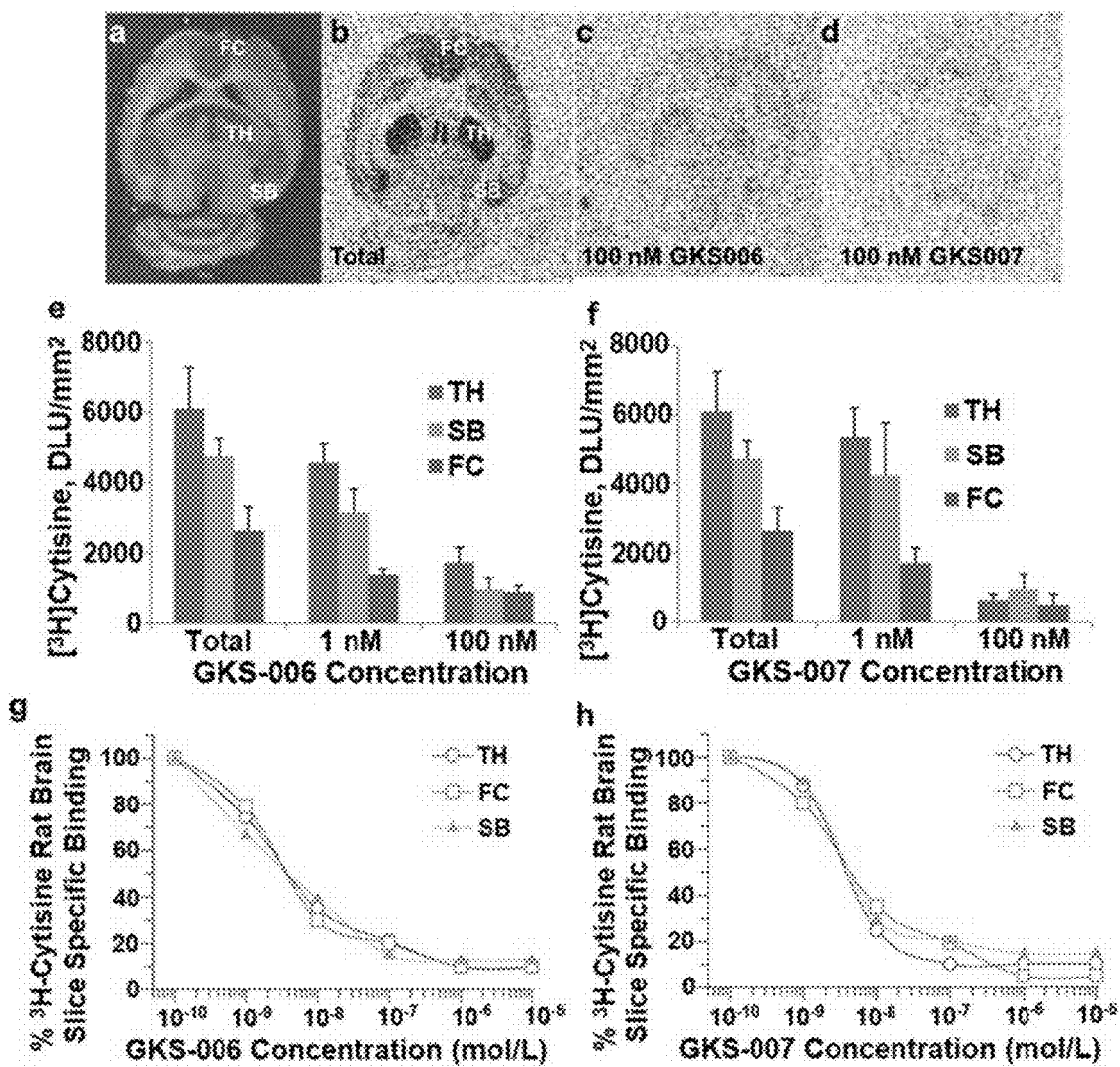
FIG. 12A-H

MULTI-TARGETING AGENTS FOR ALZHEIMER'S DISEASE THERAPY

CROSS REFERENCE TO RELATED APPLICATIONS

This application claims priority under 35 U.S.C. § 119 from Provisional Application Ser. No. 62/774,105 filed Nov. 30, 2018, the disclosure of which is incorporated herein by reference.

STATEMENT OF GOVERNMENT SUPPORT

This invention was made with Government support under Grant No. AG029479, awarded by the National Institutes of Health. The Government has certain rights in the invention.

TECHNICAL FIELD

The disclosure provides for multi-targeting agents that assist in the targeted removal of amyloid beta plaques from the brain and surrounding vasculature of subjects with Alzheimer's disease, and methods of treatment thereof.

BACKGROUND

Alzheimer's disease (AD) is a neurodegenerative disease characterized by the accumulation of β-amyloid plaques (or senile plaques, SP) and neurofibrillary tangles (NFT) in the brain. Over the last few years efforts on diagnostic methods for plaques and more recently on NFT using PET have made significant progress. With increasing efforts to find treatments and cure for AD, imaging plaques and NFT can contribute to the diagnosis and clinical management of AD. Emphasis is now on finding improved treatment strategies for AD. Currently, the only FDA approved drugs for AD treatment include acetylcholinesterase inhibitors (AChEI) such as donepezil which may be supplemented with memantine. These drugs lessen symptoms of memory loss and confusion.

SUMMARY

Alzheimer's disease (AD) affects 10% of people older than 65 and is characterized by a progressive loss of cognitive function with an abnormal accumulation of amyloid beta (Aβ) plaques and neurofibrillary tangles (NFT) in the brain. Efforts to reduce brain Aβ plaques continue to be investigated as a therapeutic approach for AD. Provided herein are the development of multiple classes of multi-targeting agents (e.g., Aβ plaque/P-gp and Aβ plaque/α4β2* nAChR) in an effort to provide innovative approaches to help remove Aβ plaques from the AD brain. The studies presented herein show that the multi-targeting agents of the disclosure maintain affinity for their respective targets.

In a particular embodiment, the disclosure provides for a multi-targeting agent that assists in the targeted removal of amyloid beta plaques from a brain and surrounding vasculature, comprising: an amyloid beta (Aβ) plaque targeting agent that exhibits moderate to high binding affinity to Aβ plaques; an Aβ plaque targeting removal agent which assists or promotes removal of Aβ plaques from a brain and surrounding vasculature; wherein, the Aβ plaque targeting agent is linked directly to the Aβ plaque targeting removal agent via a covalent bond or linked indirectly to the Aβ plaque targeting removal agent via the use of a covalently attached linker. In a further embodiment of any embodiment presented herein, the Aβ plaque targeting agent comprises the structure of Formula Formula (I)

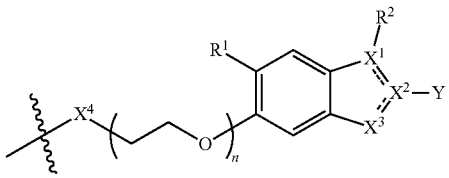

or a pharmaceutical acceptable salt, solvate or prodrug thereof, wherein, Y is selected from:

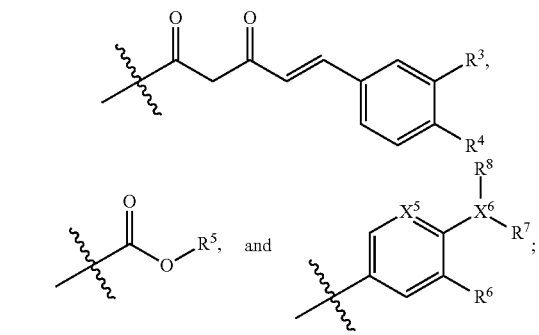

$X^1$, $X^2$, $X^5$ and $X^6$ are each independently selected from N and C; $X^3$ is selected from H, O, S, N, NH, CH, and $CH_2$; $X^4$ is selected from —O—, and —$NR^9$—; n is an integer selected from 0, 1, 2, or 3; $R^1$, $R^3$, and $R^4$ are each independently selected from H, —OH, and —$OCH_3$; $R^2$, $R^5$, $R^7$ and $R^8$ are each independently selected from H, halo, hydroxyl, a ($C_1$-$C_3$)alkyl, and a —C(O)—($C_1$-$C_3$)alkyl, wherein the($C_1$-$C_3$)alkyl, and the —C(O)—($C_1$-$C_3$)alkyl may further comprise one or more substitutions selected from halo, hydroxyl, amine, and a ($C_1$-$C_3$)alkoxy; $R^6$ is H or a halo; and $R^9$ is an H or a ($C_1$-$C_3$)alkyl. In yet a further embodiment of any embodiment presented herein, the Aβ plaque targeting agent comprises a structure selected from:

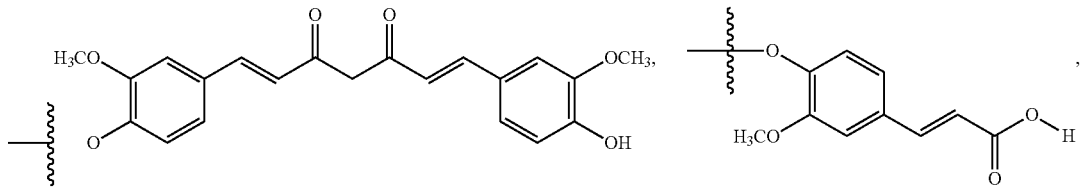

-continued
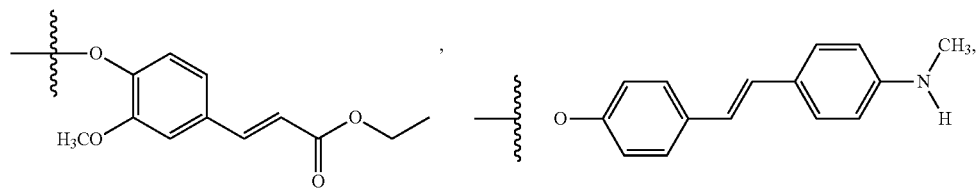
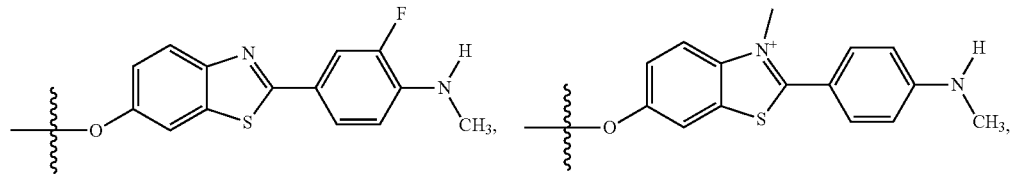
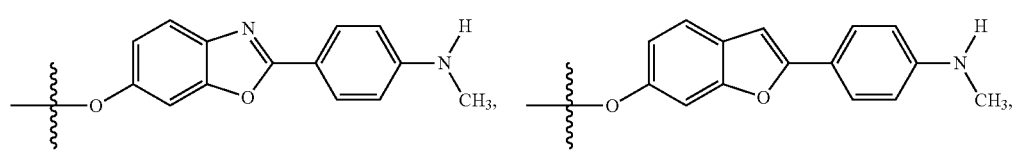
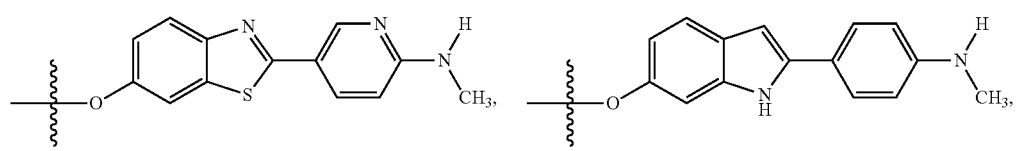
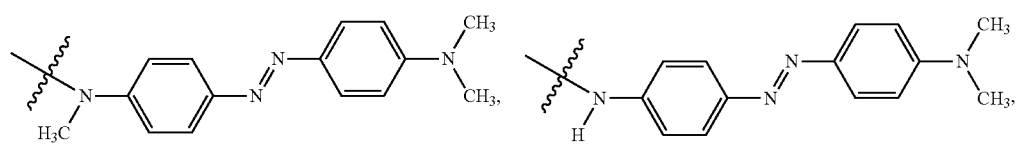
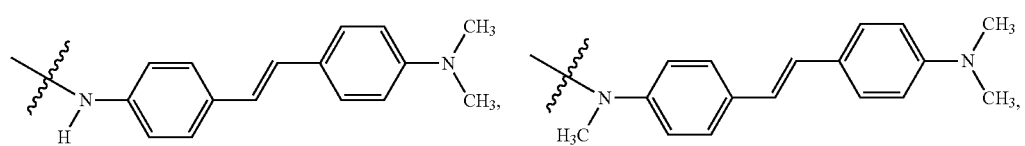
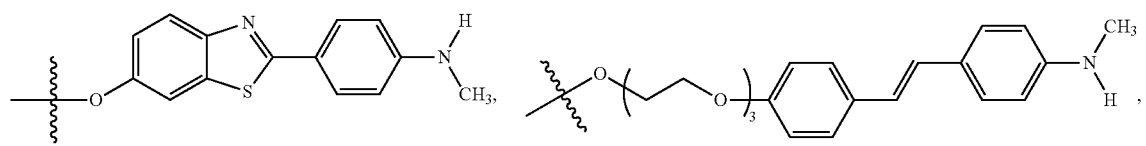
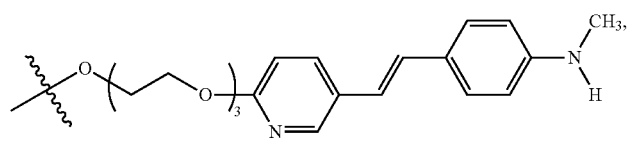
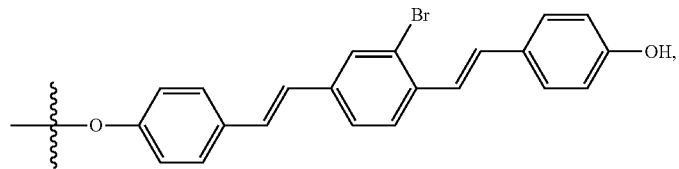
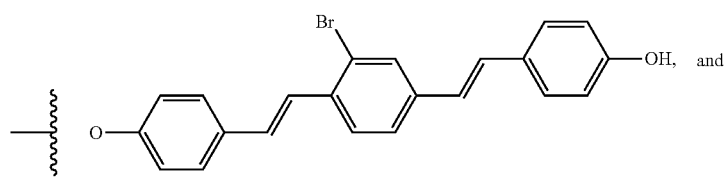

-continued

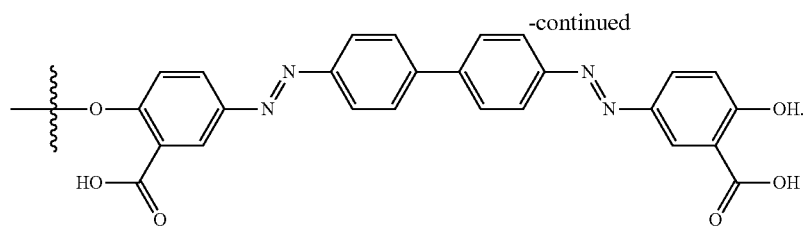

In yet a further embodiment of any embodiment presented herein, the Aβ plaque targeting agent comprises a structure selected from:

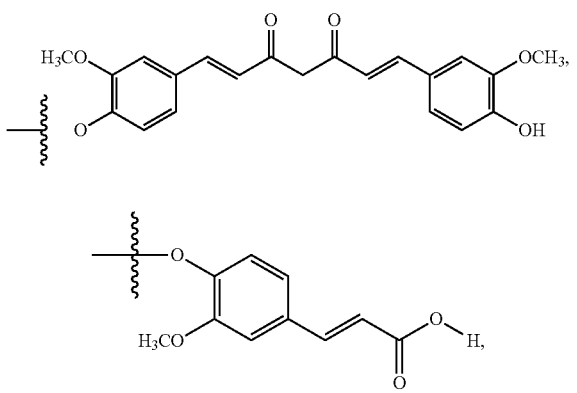

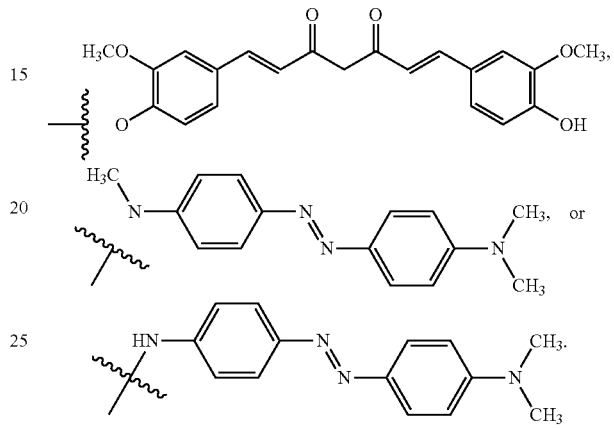

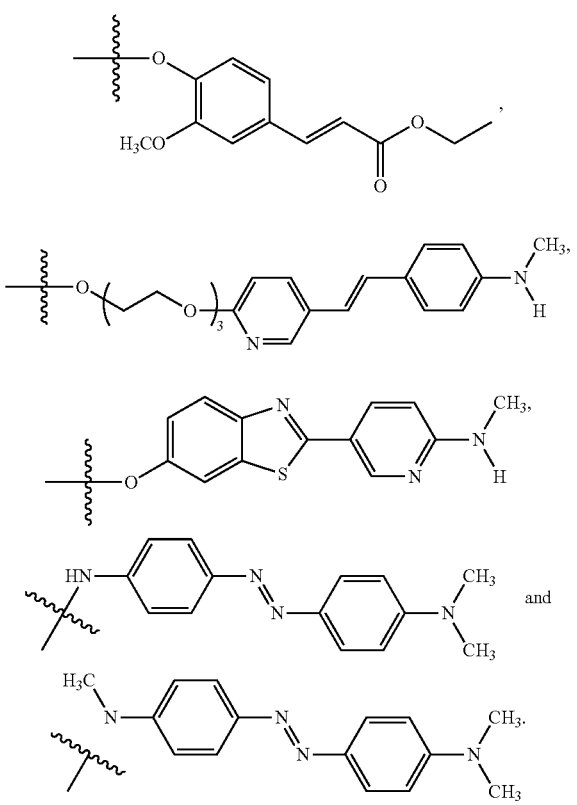

In yet a further embodiment of any embodiment presented herein, the Aβ plaque targeting agent comprises the structure of:

In yet a further embodiment of any embodiment presented herein, the Aβ plaque targeting removal agent is a substrate, inhibitor or inducer for p-glycoprotein (P-gp). Examples of such P-gp substrates, include but are not limited to, colchicine, ciclosporin, dabigatran, digoxin, diltiazem, fexofenadine, indinavir, morphine, and sirolimus. Examples of P-gp inhibitors include, but are not limited to, amiodarone, clarithromycin, ciclosporin, colchicine, diltiazem, erythromycin, felodipine, ketoconazole, lansoprazole, omeprazole, nifedipine, paroxetine, reserpine, saquinavir, sertraline, quinidine, tamoxifen, verapamil, duloxetine, elacridar, CP 100356, aosuquidar, tariquidar, valspodar and reversan. Examples of P-gp inducers include, but are not limited to, carbamazepine, dexamethasone, doxorubicin, nefazodone, phenobarbital, phenytoin, prazosin, rifampicin, St. John's wort, tenofovir, tipranavir, trazodone, and vinblastine. In yet a further embodiment of any embodiment presented herein, the Aβ plaque targeting removal agent comprises fexofenadine, verapamil, or a derivative thereof. In yet a further embodiment of any embodiment presented herein, the Aβ plaque targeting removal agent is a ligand for nicotinic α4β2 receptors. In yet a further embodiment of any embodiment presented herein, the Aβ plaque targeting removal agent is selected from 2-F-A85380, 5-I-A85380, Nifene, Nifzetidine Nifrolidine, Nifrolene, Niodene, Niofene, Venlafaxine, ASEM or a derivative of any of the foregoing. In yet a further embodiment of any embodiment presented herein, the Aβ plaque targeting removal agent is Nifrolidine or a derivative thereof. In yet a further embodiment of any embodiment presented herein, the Aβ plaque targeting agent is linked indirectly to the Aβ plaque targeting removal agent via the use of a covalently attached optionally substituted ($C_2$ to $C_{10}$)-alkyl linker, or an optionally substituted ($C_2$ to $C_{10}$)-alkoxy linker. In yet a further embodiment of any embodiment presented herein, the ($C_2$ to $C_{10}$)alkyl linker or the ($C_2$ to $C_{10}$)-alkoxy linker comprises terminal functional groups that can undergo coupling reactions with the Aβ plaque targeting agent and with the Aβ plaque targeting removal agent. In yet a further embodiment of any embodiment presented herein, the ($C_2$ to $C_{10}$)alkyl linker or the ($C_2$ to $C_{10}$)-alkoxy linker is selected from 1-amino-4-butanol, ethylene glycol, diethylene glycol, diglycolamine, —$(CH_2)_w$O$(CH_2)_x$NH—, —$(CH_2CH_2O)_yCH_2CH_2$NH—, —$(CH_2)_z$NH—, and triglycolamine, wherein w, x, y and z are each integers independently selected from 1, 2, 3, 4, 5, 6, 7, 8, 9, and 10, or a range that includes or is between any two of the foregoing integers. In yet a further embodiment of any embodiment presented herein, the multi-targeting targeting agent has a structure selected from the group consisting of:

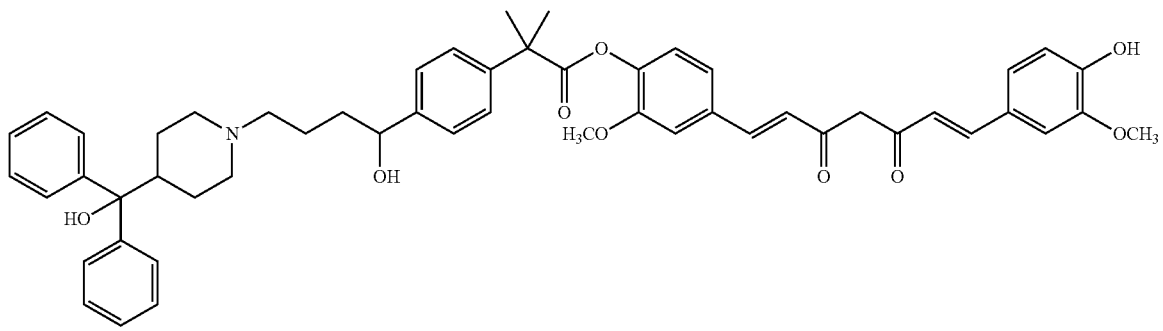

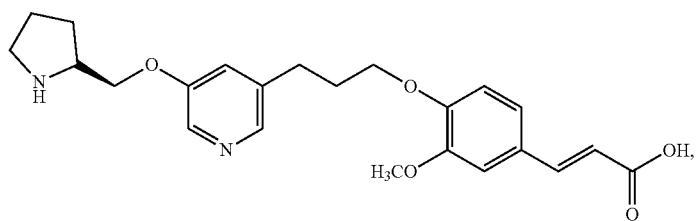

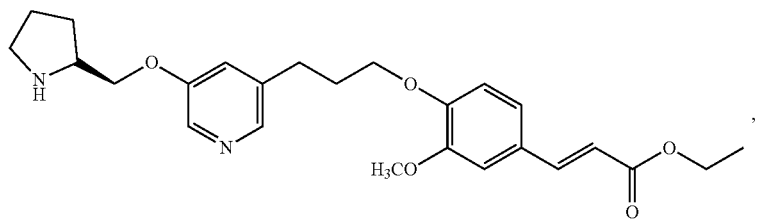

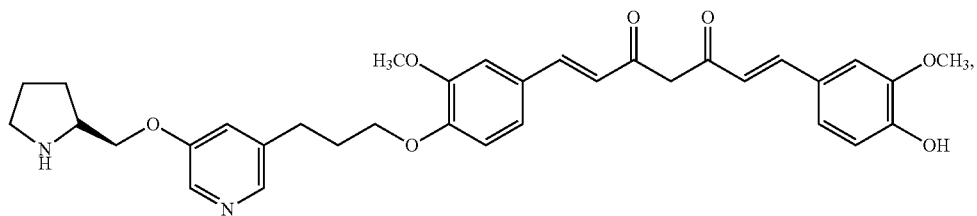

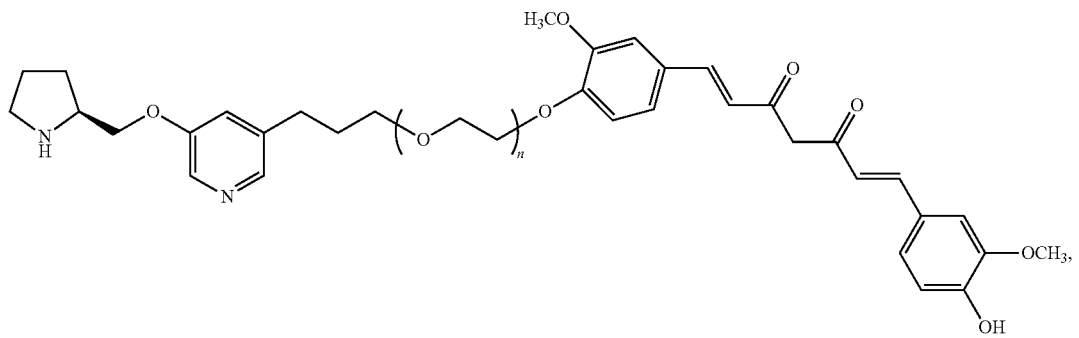

-continued

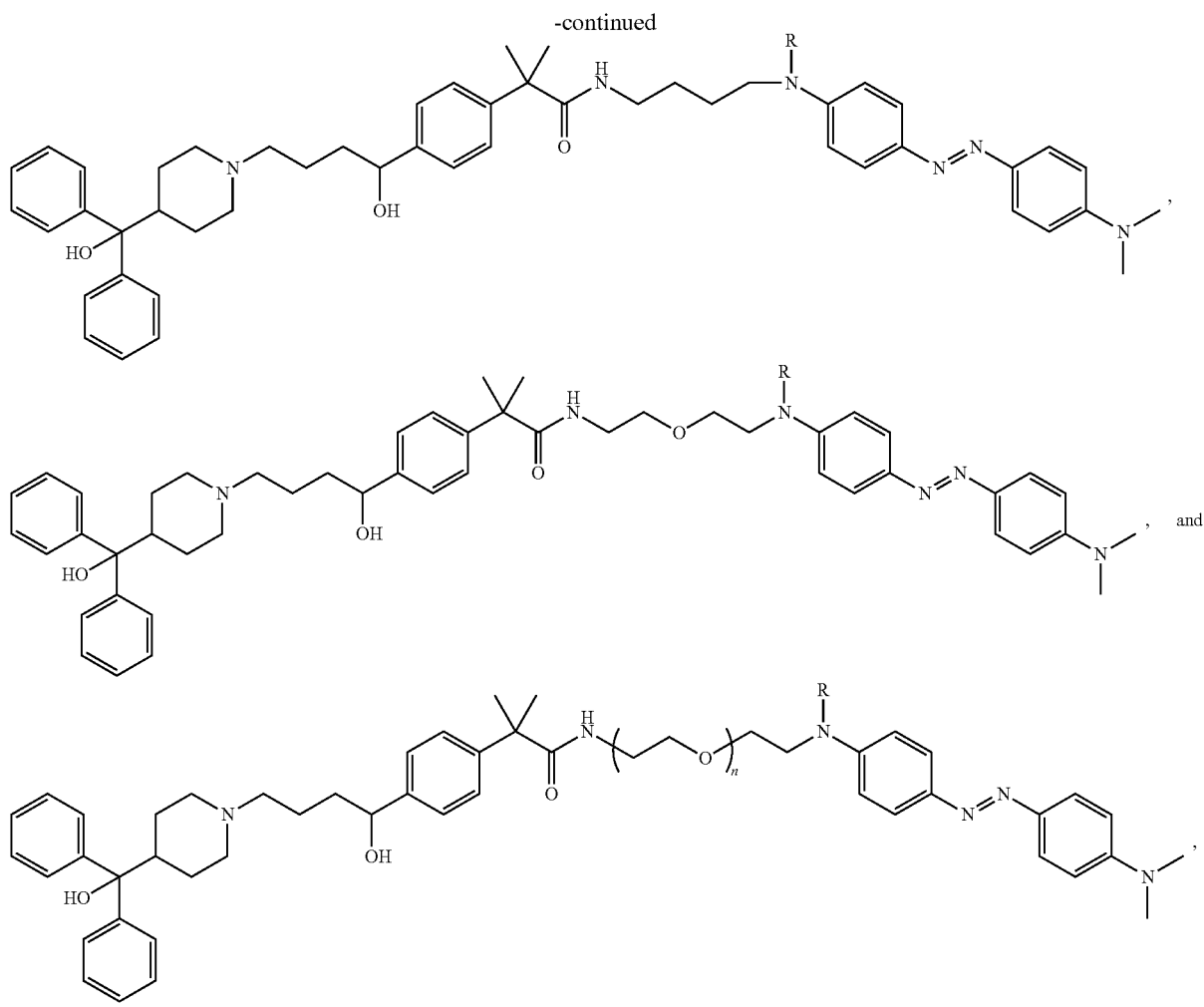

wherein, R is H or —CH$_3$; and n is an integer selected from 1, 2, 3, 4, 5, 6, 7, 8, 9, and 10, or a range that includes or is between any two of the foregoing integers.

In a particular embodiment, the disclosure also provides a pharmaceutical composition comprising a multi-targeting agent disclosed herein. In yet a further embodiment, the pharmaceutical composition is formulated for oral or parenteral delivery.

In a certain embodiment, the disclosure further provides a method of treating a subject with Alzheimer's disease, comprising: administering a therapeutically effective amount of a pharmaceutical composition or a multi-targeting agent disclosed herein. In another embodiment, a method disclosed herein further comprises the step of: administering concomitantly or sequentially to the subject effective amounts of one or more Alzheimer's treatments selected from the group consisting of cholinesterase inhibitors, antidepressants, anxiolytics, antipsychotic medications, tricyclic antidepressants, benzodiazepines, sleeping pills, atypical antipsychotics, memantine and haloperidol.

In a particular embodiment, the disclosure also provides a method of clearing Aβ plaques from a subject with Alzheimer's disease comprising: administering a therapeutically effective amount of the pharmaceutical composition of claim 15 to the subject. In another embodiment, a method disclosed herein further comprises the step of: administering concomitantly or sequentially to the subject effective amounts of one or more Alzheimer's treatments selected from the group consisting of cholinesterase inhibitors, antidepressants, anxiolytics, antipsychotic medications, tricyclic antidepressants, benzodiazepines, sleeping pills, atypical antipsychotics, memantine and haloperidol.

DESCRIPTION OF DRAWINGS

FIG. 1 presents exemplary structures of multi-targeting agents of the disclosure.

FIG. 2A-D presents the multi-agent hypothesis. (A) Aβ-binding agents, ferulic acid (FA), ferulic acid ethyl ester (FAEE), and curcumin (CUR) entering and leaving the Alzheimer's disease (AD) brain. (B) Multi-agent of FA, CUR or DAZA with p-glycoprotein (P-gp) substrate, fexofenadine (FEX) assist in towing the Aβ plaques out of brain and brain vasculature in the AD brain. (C) Aβ-binding agents, FA, FAEE or CUR entering and leaving the AD brain. (D) Multi-agent of FA, FAEE or CUR and nicotinic receptor binding agent, nifrolidine (NIF) entering the brain and NIF acting as an anchor to prolong effects of FA in the AD brain.

FIG. 7 provides for the synthesis of DAZA-N-Butyl-Fexofenadineamide (DAZA-BuNH-FEX).

FIG. 8 provides for the synthesis of DAZA-PEG1NH-Fexofenadineamide (DAZA-PEG1NH-FEX) and Mass Spectra Characterization.

FIG. 9 provides for the synthesis of DAZA-PEG2NH-Fexofenadineamide (DAZA-PEG2NH-FEX) and Mass Spectra Characterization.

FIG. 10A-G demonstrates human amyloid plaque binding of Aβ-P-gp agents. (A) Human AD brain frontal cortex autoradiograph, 10 μm thick showing gray matter (GM) and white matter (WM) binding of [$^3$H]PIB autoradiograph. (B)-(E) [$^3$H]PIB autoradiographs in adjacent brain slices in the presence of 10 μM FA, KD-003, CUR-FEX and CUR, respectively. (F) Quantitation of [$^3$H]PIB in GM and WM regions in experiments (A)-(E). (G) Ratio of GM to WM in experiments (A)-(E).

FIG. 11A-G presents human amyloid plaque binding of Aβ-nAChR agents. (A) Scan of 10 μm thick human AD brain frontal cortex, showing gray matter (GM) and white matter (WM). (B) [$^3$H]PIB autoradiograph in the brain slice showing GM (arrow) and WM. (C)-(E) [$^3$H]PIB autoradiographs in adjacent brain slices in the presence of 1 μM TAZA, FA and GKS-007, respectively. (F) Quantitation of [$^3$H]PIB in GM and WM regions in experiments (B)-(E). (G) Ratio of GM to WM in experiments (B)-(E).

FIG. 12A-H Rat brain nicotine receptor binding of Aβ-α4β2* agents. (A) Scan of 10 μm thick rat brain slice; (B) Total binding autoradiograph of [$^3$H]cytisine in different brain regions (FC frontal cortex, SB subiculum, TH thalamus); (C) Autoradiograph of [$^3$H]cytisine in the presence of 100 nM GKS-006; (D) Autoradiograph of [$^3$H]cytisine in the presence of 100 nM GKS-007; (E) Displacement of [$^3$H] cytisine in the presence of 1 nM and 100 nM GKS-006. (F) Displacement of [$^3$H]cytisine in the presence of 1 nM and 100 nM GKS-007. (G) Competition specific binding curves of GKS-006 with [$^3$H]cytisine binding in rat brain regions shown in (B). (H) Competition specific binding curves of GKS-007 with [$^3$H]cytisine binding in rat brain regions shown in (B).

DETAILED DESCRIPTION

Figure 3:
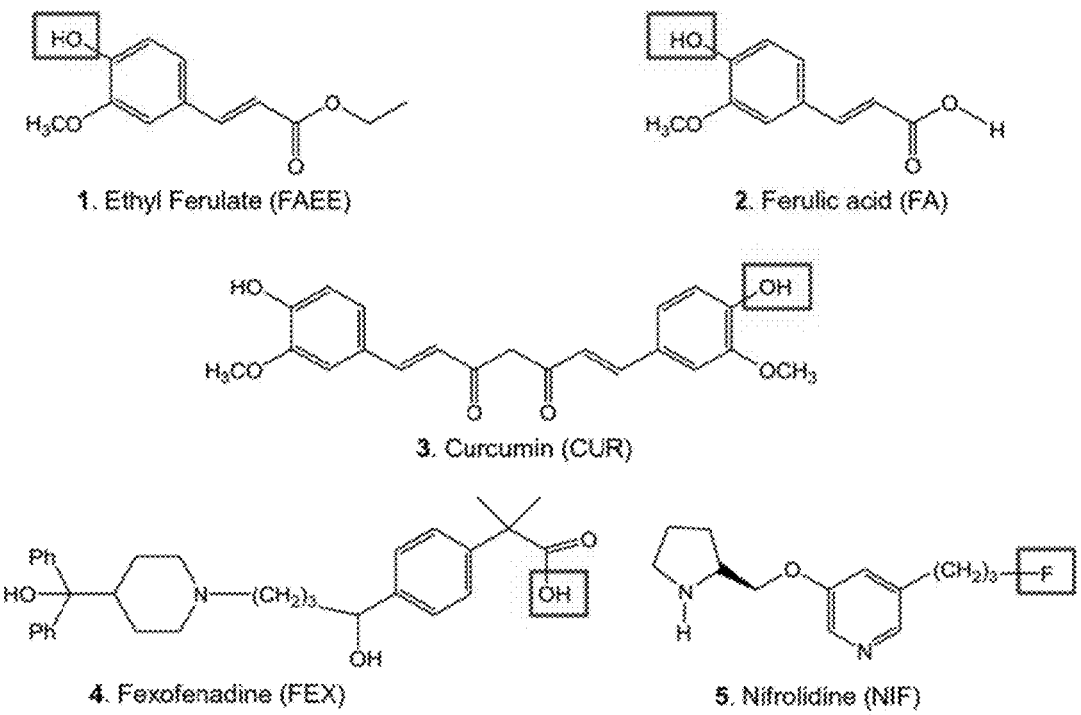
FIG. 3 presents chemical structures of compounds referred herein. Amyloid β-binding agents, ferulic acid ethyl ester (FAEE) 1, ferulic acid 2, curcumin 3, P-glycoprotein substrate fexofenadine 4, α4β2* nicotinic acetylcholinergic receptor agent, nifrolidine 5. Blue boxes show the functional groups used to make the multi-agents

As used herein and in the appended claims, the singular forms "a," "an," and "the" include plural referents unless the context clearly dictates otherwise. Thus, for example, reference to "a targeting agent" includes a plurality of such targeting agents and reference to "the nicotinic a4b2 receptor ligand" includes reference to one or more nicotinic a4b2 receptor ligands and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

The term "alkenyl", refers to an organic group that is comprised of carbon and hydrogen atoms that contains at least one double covalent bond between two carbons. Typically, an "alkenyl" as used in this disclosure, refers to organic group that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. While a $C_2$-alkenyl can form a double bond to a carbon of a parent chain, an alkenyl group of three or more carbons can contain more than one double bond. In certain instances, the alkenyl group will be conjugated, in other cases an alkenyl group will not be conjugated, and yet other cases the alkenyl group may have stretches of conjugation and stretches of nonconjugation. Additionally, if there is more than 2 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkyl", refers to an organic group that is comprised of carbon and hydrogen atoms that contains single covalent bonds between carbons. Typically, an "alkyl" as used in this disclosure, refers to an organic group that contains 1, 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. While a $C_2$-alkynyl can form a triple bond to a carbon of a parent chain, an alkynyl group of three or more carbons can contain more than one triple bond. Where if there is more than 3 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 5 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. The term generally represented by the notation "$C_x$-$C_y$" (where x and y are whole integers and y>x) prior to a functional group, e.g., "$C_1$-$C_{12}$ alkyl" refers to a number range of carbon atoms. For the purposes of this disclosure any range specified by "$C_x$-$C_y$" (where x and y are whole integers and y>x) is not exclusive to the expressed range, but is inclusive of all possible ranges that include and fall within the range specified by "$C_x$-$C_y$" (where x and y are whole integers and y>x). For example, the term "$C_1$-$C_4$" provides express support for a range of 1 to 4 carbon atoms, but further provides implicit support for ranges encompassed by 1 to 4 carbon atoms, such as 1 to 2 carbon atoms, 1 to 3 carbon atoms, 2 to 3 carbon atoms, 2 to 4 carbon atoms, and 3 to 4 carbon atoms.

The term "cycloalkenyl", as used in this disclosure, refers to an alkene that contains at least 4 carbon atoms but no more than 12 carbon atoms connected so that it forms a ring. A "cycloalkenyl" for the purposes of this disclosure encompasses from 1 to 4 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompasses from 1 to 4 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "substituent" refers to an atom or group of atoms substituted in place of a hydrogen atom, e.g., a boronic acid group. For purposes of this invention, a substituent would include deuterium atoms. Examples of substituents include, but are not limited to, halo (e.g., F, Cl, Br or I), optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, and boronic ester). Further examples of substituents include, but are not limited to, aryl, heterocycle, alkyl, heteroalkyl, alkenyl, heteroalkenyl, alkynyl, heteroalkynyl, cycloalkyl, alkoxy, ester, halo, hydroxyl, anhydride, carbonyl, carboxyl, carbonate, carboxylate, aldehyde, boronic acid, boronic ester, haloformyl, ester, hydroperoxy, peroxy, ether, orthoester, carboxamide, amine, imine, imide, azide, azo, cyanate, isocyanate, nitrate, nitrite, isonitrile, nitroso, nitro, nitrosooxy, pyridyl, sulfide, disulfide, sulfinyl, sulfo, thiocyanate, isothiocyanate, carbonothioyl, phosphino, phosphono, and phosphate.

The term "substituted" with respect to hydrocarbons, heterocycles, and the like, refers to structures wherein the parent chain contains one or more substituents.

The term "unsubstituted" with respect to hydrocarbons, heterocycles, and the like, refers to structures wherein the parent chain contains no substituents.

The term "co-administration" or administration "in combination," as used herein, refers to two or more agents being found in the patient's bloodstream at the same time, regardless of when or how they are actually administered. In one embodiment, the agents are administered simultaneously. In another embodiment, administration in combination is accomplished by combining the agents in a single dosage form. In yet another embodiment, the agents are administered sequentially. In a further embodiment the agents are administered through the same route. For example, in some embodiments, both agents are administered orally. In yet a further embodiment, the agents are administered through different routes. For example, in one embodiment, one agent is administered orally and the other agent is administered i.v.

The terms "patient", "subject" and "individual" are used interchangeably herein, and refer to an animal, particularly a human, to whom treatment including prophylaxis treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g., mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. "Mammal" refers to any animal classified as a mammal, including humans, non-human primates, domestic and farm animals, and zoo, sports, or pet animals, such as dogs, cats, cattle, horses, sheep, pigs, goats, rabbits, etc. Patient or subject includes any subset of the foregoing, e.g., all of the above, but excluding one or more groups or species such as humans, primates or rodents. A subject can be male or female. A subject can be a fully developed subject (e.g., an adult) or a subject undergoing the developmental process (e.g., a child, infant or fetus).

The term "therapeutically effective amount" as used herein, refers to an amount that is sufficient to affect a therapeutically significant reduction in one or more symptoms of the condition when administered to a typical subject who has the condition. A therapeutically significant reduction in a symptom is, e.g., about 10%, about 20%, about 30%, about 40%, about 50%, about 60%, about 70%, about 80%, about 90%, about 100%, or more as compared to a control or non-treated subject.

The term "treat" or "treatment" as used herein, refers to a therapeutic treatment wherein the object is to eliminate or lessen a condition or a symptom. Beneficial or desired clinical results include, but are not limited to, elimination of symptoms or a condition, alleviation of symptoms or a condition, diminishment of extent of the condition or symptom, stabilization (i.e., not worsening) of the state of the condition or symptom, and delay or slowing of progression of the condition or symptoms.

Alzheimer's disease (AD) affects 10% of people older than 65 and is characterized by a progressive loss of cognitive function with an abnormal accumulation of amyloid β (Aβ) plaques and neurofibrillary tangles (NFT) in the brain. Reduction in the accumulation of Aβ plaques and NFT continues to be investigated as therapeutic approaches for AD. Although the NFT hypothesis is being sought after as a better indicator of clinical AD, Aβ plaque is still being pursued and efforts have been made to remove Aβ plaques in AD patients using antibodies. Current approaches underway as AD treatments involve attempts to decrease the plaque load in the brain either by removal of the Aβ plaques (using antibodies, curcumin analogs and ultrasound) or decrease the production (using secretase inhibitors) of the Aβ plaques in the brain (see Table 1). Large clinical trials were carried out with anti-amyloid monoclonal antibodies, bapineuzumab (see Table 1 at 2) and solanezumab see Table 1 at 3). Both of these trials did not improve clinical outcome and importantly the Aβ plaque load (measured by PET imaging) did not change significantly before and after antibody treatment. A different approach currently underway is to reduce the production of Aβ peptide by inhibition of the two secretases enzymes (γ- and β-) which cleave the amyloid precursor protein (APP) (see Table 1 at 4). The γ-secretase inhibitors have an adverse effect on notch signaling pathway and were therefore not found to be suitable for further development. Development of γ-secretase inhibitors are being pursued, although some of them have been discontinued due to liver toxicity. The natural product curcumin and its analogs continue to be investigated for their anti-inflammatory and anti-amyloidogenic properties (see Table 1 at 5) but concerns remain about efficacy in humans and brain bioavailability.

TABLE 1

Brief Summary of Therapeutic Agents being used Alzheimer's Disease (Human and Animal Models)

| # | Therapeutic Agent | Target | Subjects | Outcome |
|---|---|---|---|---|
| 1 | AChEI, Memantine | Acetylcholine levels; NMDA receptors | All stages | Lessen symptoms of memory loss and confusion |
| 2 | Bapineuzumab | Anti-Amyloid β monoclonal antibody | Mild to moderate AD | Did not improve clinical outcomes |
| 3 | Other antibodies (Solanezumab) | Anti-Amyloid β monoclonal antibody | Mild to moderate AD | Did not improve clinical outcomes. Trials continue in early stage of disease |
| 4 | Secretase Inhibitors | β-Secretase enzymes to reduce Aβ peptide | MCI, AD and rodent models | Liver toxicity; impaired cognition in animals. |
| 5 | Curcumin analogs | Aβ Plaques | Transgenic Mice; Human AD | Mice studies promising in reducing Aβ Plaques; human outcome uncertain |
| 6 | Ultrasound | Blood brain barrier (BBB) opening | Transgenic Mice | Decrease in brain Aβ Plaques; improved memory task |

Transgenic mice have greatly accelerated the understanding of the mechanisms of neurodegeneration underlying AD and development of therapeutics that may slow, halt and potentially reverse AD. Immunization with fibrillar Aβ in young transgenic mice overexpressing mutant human APP can prevent subsequent plaque development. A number of therapeutic agents have been tested, such as nonsteroidal anti-inflammatory drugs, antioxidants and statins in transgenic mice. Although they provide insights on AD treatment, translation to humans has not occurred. More recently, scanning ultrasound was repeatedly used on the mouse brain to make the BBB leaky for Aβ removal (Table 1 at 6). Adaptation of this method to human use may pose a challenge. No efforts to remove Tau products from the brain have been made heretofore.

There is increasing evidence of the presence of ventricular clearance pathways such as the paravascular (or also referred as glymphatic) pathway and olfactory lymphatic pathway which may be involved in clearing macromolecules from the brain. Specific proteins such as aquoporin4 have been identified that may play an important role in the movement of water containing macromolecules. Insufficient clearance of macromolecules such as Aβ results in formation of Aβ fibrils and plaques in the brain. Down regulation of P-gp has been reported in AD and upregulation of P-gp using rifampicin and caffeine were found to increase clearance of Aβ from the brain. In normal human plasma a soluble form of lipoprotein receptor related protein (LRP1) is a major endogenous brain Aβ 'sinker' that sequesters up to 90% of plasma Aβ peptides. In AD the levels and capacity of LRP1 are reduced which increases free Aβ fraction in plasma. This in turn may increase brain Aβ burden through decreased Aβ efflux and/or increased Aβ influx across the BBB. To what extent these efflux pathways along with P-gp may be involved in removal of the larger Aβ products (oligomers, fibrils and plaques) from the brain is currently not known.

Provided herein is the development of multi-targeting agents for Aβ plaque removal in an Alzheimer's disease brain comprising an Aβ plaque target agent that is linked to a second target agent to assist in removal of the plaque from the brain and surrounding vasculature (e.g., see FIG. 2). The disclosure further provides for the evaluation of multi-targeting agents with substrate affinity for P-gp and high affinity for Aβ plaque (P-gp-Aβ binding molecule) that may be able to bind to Aβ and which be effluxed out of the brain by P-gp using the paravascular (or glymphatic) pathways and olfactory lymphatic pathways (e.g., see FIG. 2B).

Figure 16:
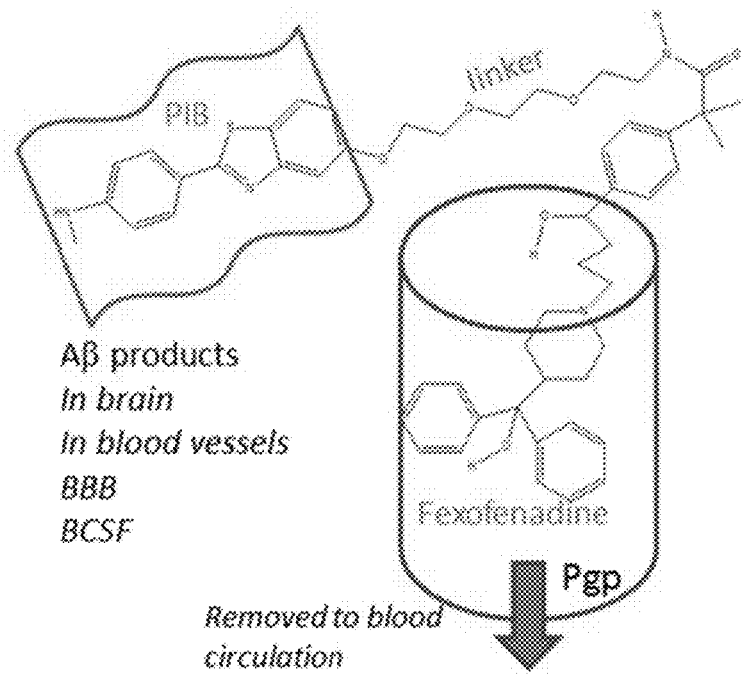
FIG. 16 presents a schematic of a pathway for PIB-diglycolamine-fexofenadine at P-gp.

The glymphatic pathway consisting of aquaporin4 along with the receptors for Aβ transport across the blood-brain barrier (BBB) from brain to blood LRP1, receptor for advanced glycation end products (RAGE) and P-gp play a major role in the efflux of Aβ. P-glycoprotein (P-gp) has been shown to efflux macromolecules across the blood brain barrier (BBB) and blood-cerebrospinal fluid barrier. Crystal structure of P-gp at 3.8 angstroms revealed an internal cavity of ~6000 angstroms cubed with a 30-angstrom separation of the two nucleotide-binding domains. Two additional P-gp structures with cyclic peptide inhibitors demonstrate distinct drug-binding sites in the internal cavity capable of stereoselectivity that is based on hydrophobic and aromatic interactions. It is anticipated that P-gp-Aβ multi-targeting agents may assist in the bringing Aβ products in the vicinity of BBB and BCSF as schematically shown in FIG. 16 in order for the glymphatic pathway to efflux the macromolecules.

Several substrates and inhibitors have been characterized for P-gp. Fexofenadine is an antihistamine used for allergies and is a P-gp substrate. The presence of the carboxylic acid functional group enables its easier derivatization compared to other P-gp substrates (e.g., see FIG. 3). Modification of the carboxylic acid end of fexofenadine may not have major detrimental effects on its interaction with P-gp as a substrate. The carboxylic acid group in fexofenadine was used to form either an amide bond to attach a 4-carbon chain linker to ferulic acid or alternatively it was attached directly to curcumin in a phenolic ester linkage. Energy minimized structures of fexofenadine, curcumin and the multi-agent CUR-FEX exhibited similar backbone structures suggestive of maintenance of binding properties of curcumin to Aβ amyloid (e.g., see FIG. 4). Ferulic acid, ferulic acid ethyl ester and curcumin have all been reported to bind and interact with Aβ amyloid plaques and help in the dissolution/disaggregation of the Aβ plaques. Accordingly, in a particular embodiment, a suitable P-gp-Aβ multi-binding agent of disclosure comprises at least the following three features: (1) use of an Aβ binding agent (e.g., ferulic acid 2 or curcumin 3); (2) use of substrate for P-gp (e.g., fexofenadine 4); and optionally, (3) use a linker (e.g., 1-amino-4-butanol) to connect the multi-Aβ binding agents. Ferulic acid ethyl ester and ferulic acid (1 and 2, FIG. 2), which are hemi-analogs of curcumin 3 have all been reported to have anti-amyloidogenic properties.

In order to enhance dissolution/disaggregation of the Aβ plaques by FAEE and FA, Aβ-multi-targeting agents were developed so as to increase the brain retention time of the agents by anchoring them to a secondary target. In another embodiment, the disclosure provides for Aβ multi-targeting agents with substrate affinity for neuronal α4β2* nicotinic cholinergic receptors (nAChRs) and high affinity for Aβ plaques (e.g., see FIG. 2D). The α4β2* nAChRs receptors are involved in learning and memory and have been implicated in human neurodegeneration, including Alzheimer's disease, and Parkinson's disease. The α4β2* nAChRs are localized in frontal cortex, cingulate, temporal cortex, subiculum and parts of the hippocampus, all of which are known to have significant amounts of Aβ plaques in AD patients. Two fluorescent probes, nifrodansyl, and nifrofam with nanomolar affinities for α4β2* nAChRs were discovered by using a PET imaging agent [$^{18}$F]NIF. Nifrofam labeling was observed in α4β2* nAChR-expressing HEK cells and was upregulated by nicotine exposure. Based on these findings, NIF was derivatized using an ether linkage (as opposed to an amide linkage in the case of nifrofam) with FAEE and FA. Fluoroalkyl derivatives, such as nifrolidine 5 were prepared as radioligands for α4β2* receptors. Derivatization of the 3-carbon chain at the 5-position in nifrolidine was found not to adversely affect the binding to the α4β2* nAChRs. In the case of the α4β2 nAChR-Aβ multi-targeting agents, it is further postulated that simultaneous action (or binding) of the multi-targeting agents to the α4β2 nAChR and the Aβ site is unlikely due to the small size of the multi-targeting agents.

Figure 6:
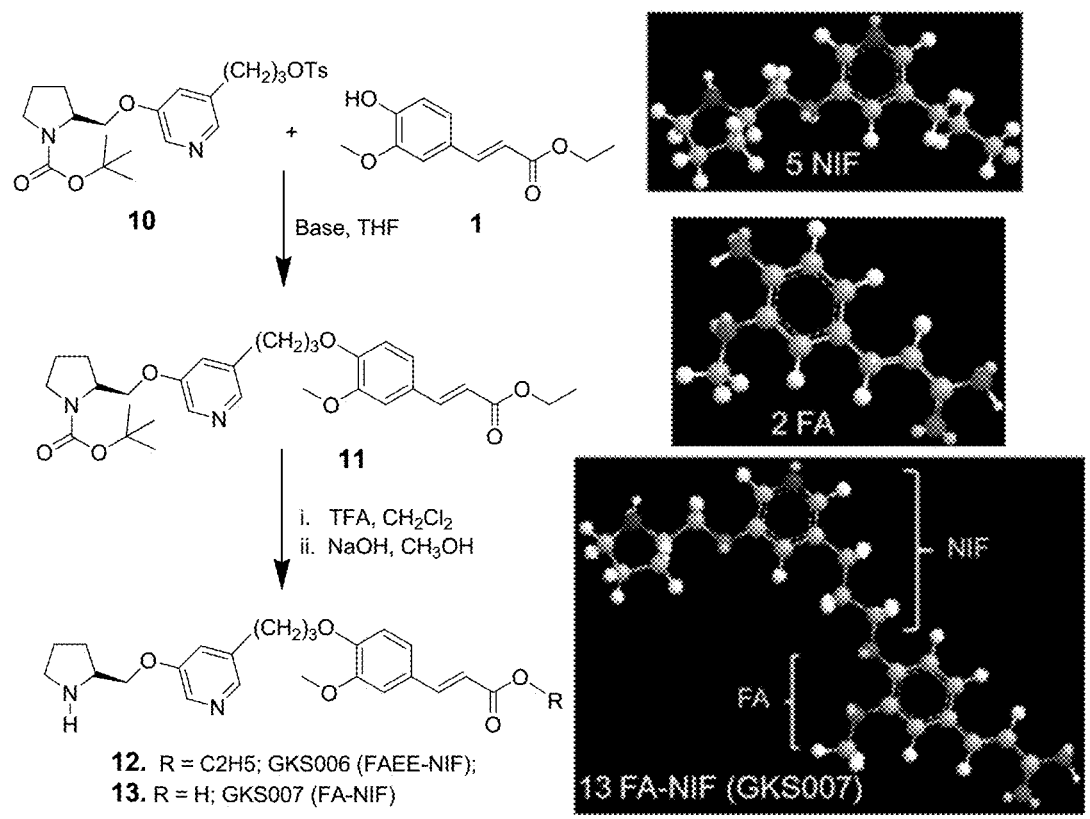
FIG. 6 provides for ferulic acid ether synthesis of Aβ-α4β2* agents. Reaction of substituted tosylate 10 and FAEE 1 (base, THF, tetrahydrofuran) to provide ether 11. Deprotection of N-BOC 11 with TFA for GKS-006 12 and base hydrolysis of 12 to provide GKS-007 13. Energy minimized models comparing the multi-agent, FA-NIF (GKS-007) 13 with FA 2 and NIF 5.
Figure 13:
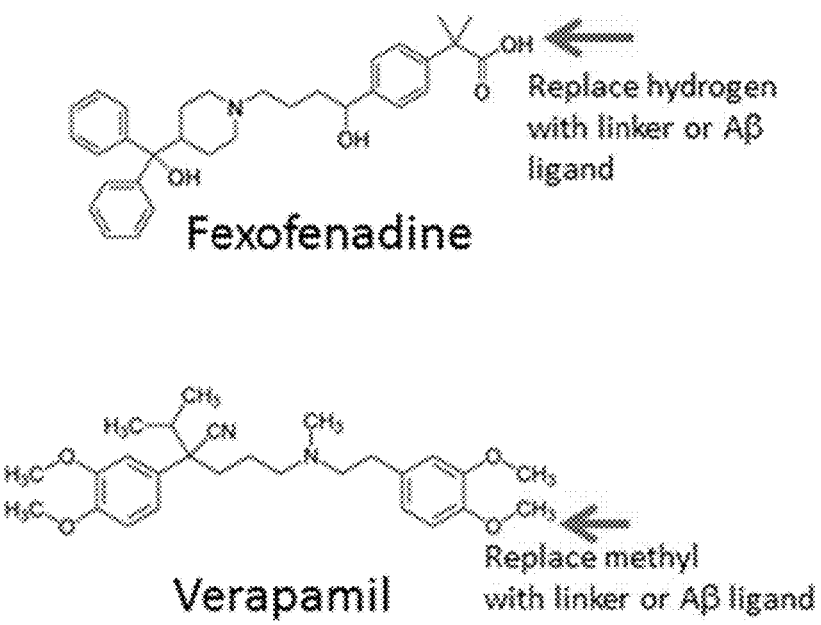
FIG. 13 presents embodiments of P-gp Substrates that can be used to produce additional Aβ multi-targeting agents of the disclosure. Chemical structures of fexofenadine and verapamil showing positions where Aβ ligand or linker is attached.

Thus, the disclosure provides in another embodiment, Aβ-multi-targeting agents which comprise a nifrolidine derivative coupled to ferulic acid ethyl ester and ferulic acid. Energy-minimized structures of NIF, FA, and the multi-targeting agent FA-NIF (GKS-007) shows retention of primary-binding features to α4β2* nAChR (e.g., see FIG. 6). This was confirmed by the high affinity measured for both GKS-006 and GKS-007 at the α4β2* nAChR sites in rat brain slices.

Additional multi-targeting agents comprising N,N-dimethyl-4,4'-azodianiline (DAZA) coupled with fexofenadine were prepared (see FIGS. 7-9). N,N,N'-trimethyl-4,4'-azodianiline (TAZA), a compound having significant structural similarity to DAZA, was shown to have high binding affinity for human Alzheimer's disease Aβ plaques (see U.S. Pat. No. 9,180,212 B2, the disclosure of which is hereby incorporated by reference in full). It is expected that multi-targeting agents comprising DAZA and TAZA would have higher binding affinities for Aβ plaques than multi-targeting agents comprising ferulic acid and ferulic acid ethyl ester. As such, the DAZA and TAZA based multi-targeting agents would be expected to enhance the ability of P-glycoprotein to efflux Aβ plaques from the Alzheimer's disease brain. Moreover, it is expected that the DAZA and TAZA based multi-targeting agents would have better in vivo stability than curcumin-fexofenadine (CUR-FEX) multi-targeting agents. The increased in vivo stability would result from the DAZA and TAZA based multi-targeting agents comprising amide linkages, instead of the more labile ester linkages of CUR-FEX.

Further, provided herein are studies looking at in vitro competition of the Aβ multi-targeting agents with [$^3$H]PIB labeled Aβ plaques in postmortem human AD brain slices; and studies looking at the measurement of in vitro binding affinities of Aβ-α4β2* nAChR agents in rat brain slices using [³H]cytisine labeled α4β2* nAChR sites. Curcumin had a significant displacement effect on the binding of [³H]PIB to the Aβ plaques in human frontal cortex (e.g., see FIG. 10). This is consistent with the binding affinity for Aβ plaques/fibrils reported for curcumin. Although binding of [³H]PIB by 10 µM curcumin was reduced by 50%, a higher degree of displacement would have been expected based on the affinity of curcumin. It is likely that the affinity of curcumin in senile plaques in human postmortem brain slices may be lower. Displacement of [³H]PIB by TAZA (e.g., see FIG. 11) was greater than observed by curcumin and is consistent with findings of the high affinity of TAZA for Aβ plaques. Compared to both curcumin and TAZA, ferulic acid exhibited little displacement of [³H]PIB, suggesting weaker affinity for Aβ plaques and is consistent with previously reported findings for ferulic acid. Of the multi-targeting agents, CUR-FEX exhibited the largest displacement of [³H]PIB (GM/WM reduced by 35%), likely due to the effect of curcumin, compared to KD003 and GSK007, which are multi-targeting agents for P-gp and α4β2* nAChR respectively, containing ferulic acid. It is likely that higher concentrations of ferulic acid and the multi-targeting agents containing ferulic acid may have a greater effect in reducing [³H]PIB binding. The mechanism of action for the foregoing results, likely arises from the slow dissociation of the curcumin dual targeting agent from the α4β2 nAChR binding site and thus slow clearance from the brain regions. This will allow for the curcumin component of the multi-targeting agent to have increased interactions with Aβ (oligomers, fibrils and plaques) in the vicinity and increase the potential for clearance. An additional mechanism of action for the multi-targeting agent is by direct action of enhancing α4β2 nAChR activity, since cholinergic deficits are known in AD.

In a particular embodiment, the disclosure provides for multi-targeting agents for Aβ plaque removal in an Alzheimer's disease brain comprising an Aβ plaque targeting agent that is linked to a second Aβ plaque removal targeting agent that assists in removal of the plaque from the brain and surrounding vasculature. In a particular embodiment, the multi-targeting agents disclosed herein comprise an Aβ plaque targeting agent having the general structure of Formula I:

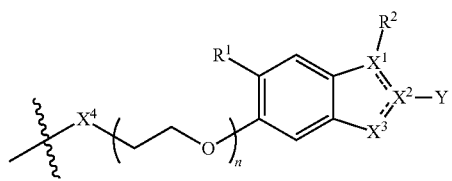

Formula (I)

or pharmaceutically acceptable salt, solvate, or prodrug thereof, wherein,

Y is selected from:

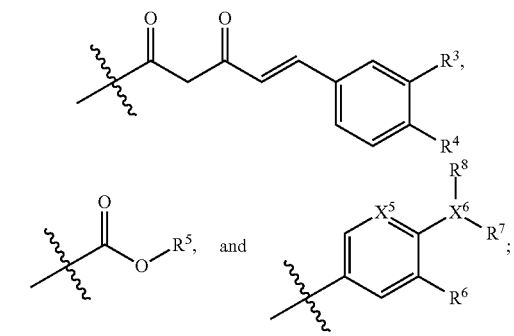

$X^1$, $X^2$, $X^5$ and $X^6$ are each independently selected from N and C;
$X^3$ is selected from H, O, S, N, NH, CH, and $CH_2$;
$X^4$ is selected from —O—, and —$NR^9$—;
n is an integer selected from 0, 1, 2, or 3;
$R^1$, $R^3$, and $R^4$ are each independently selected from H, —OH, and —$OCH_3$;
$R^2$, $R^5$, $R^7$ and $R^8$ are each independently selected from H, halo, hydroxyl, a ($C_1$-$C_3$)alkyl, and a —C(O)—($C_1$-$C_3$) alkyl, wherein the ($C_1$-$C_3$)alkyl, and the —C(O)—($C_1$-$C_3$) alkyl may further comprise one or more substitutions selected from halo, hydroxyl, amine, and a ($C_1$-$C_3$)alkoxy; and
$R^6$ is H or a halo; and
$R^9$ is an H or a ($C_1$-$C_3$)alkyl.

In a further, embodiment, the Aβ plaque targeting agent has a structure selected from one of the following:

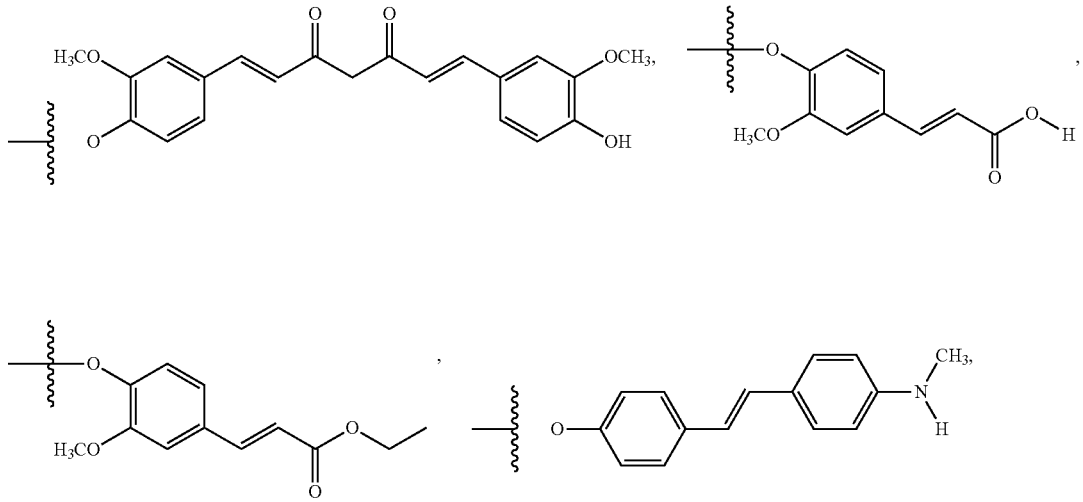

-continued
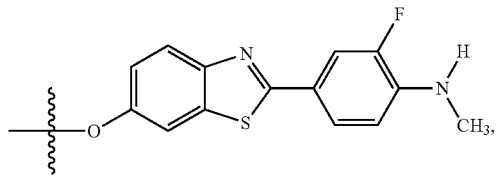
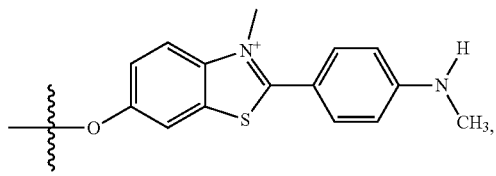
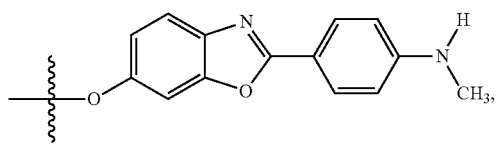
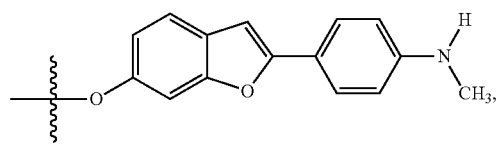
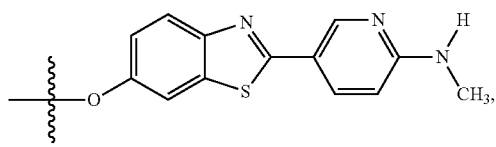
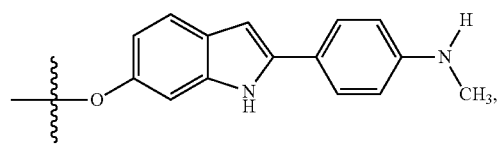
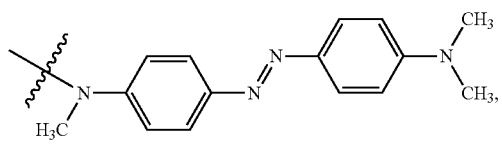
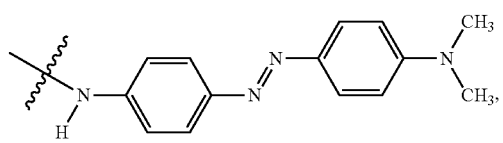
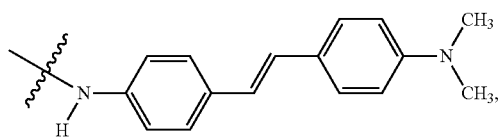
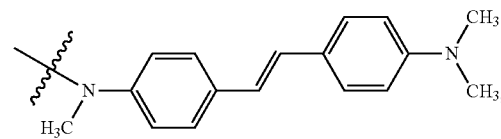
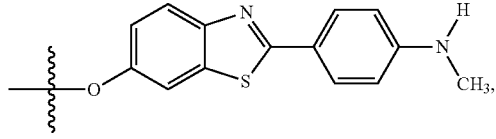
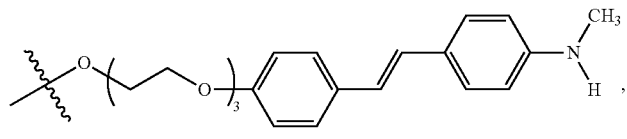
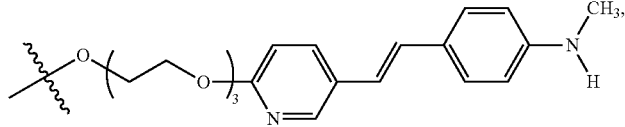
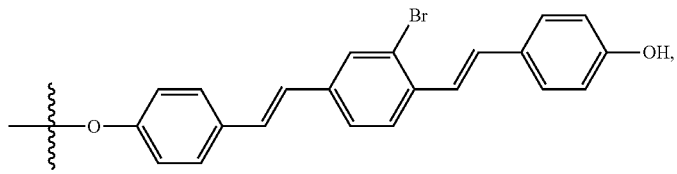
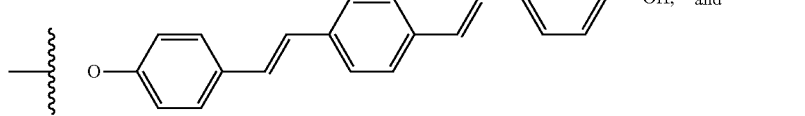, and
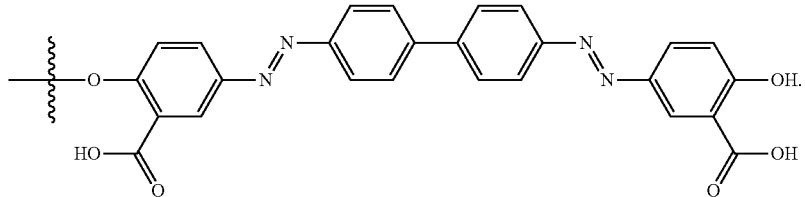

Figure 14:
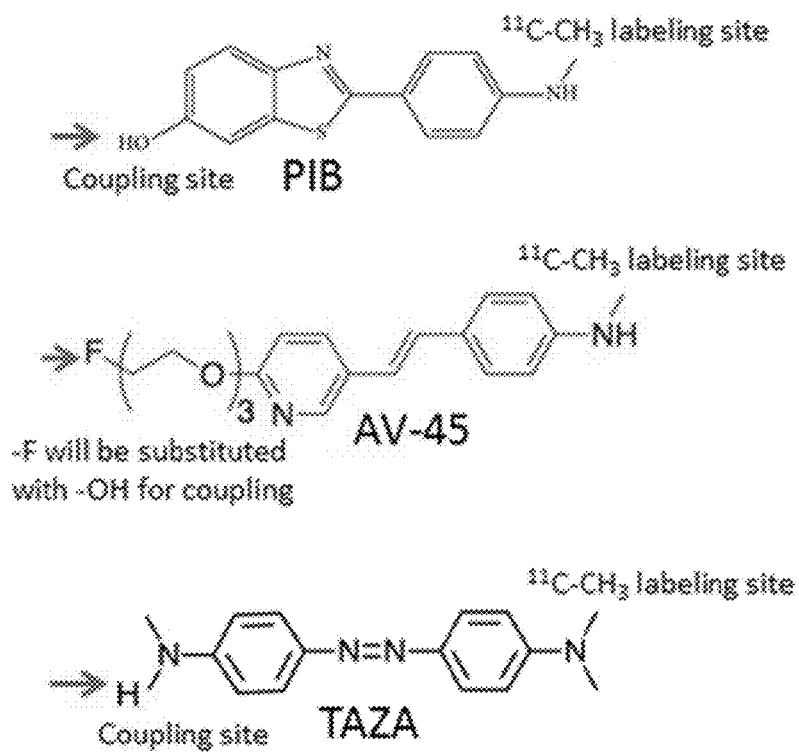
FIG. 14 presents embodiments of Aβ targeting ligands that can be used to produce additional Aβ multi-targeting agents of the disclosure. The structure of PIB showing the phenolic hydroxyl to be linked to P-gp or the linker; AV-45, the fluorine will be removed and the corresponding hydroxylated derivative will be used to couple with P-gp or the linker; TAZA showing the anilino nitrogen which will be coupled with P-gp or the linker. For radiotracer development, all three have the anilino methyl group that can be radiolabeled with $^{11}$C-methyl triflate.

Additional Aβ ligands to be considered are shown in FIG. 14: structure of PIB showing the phenolic hydroxyl to be linked to P-gp or the linker; AV-45, the fluorine will be removed and the corresponding hydroxylated derivative will be used to couple with P-gp or the linker; and TAZA showing the anilino nitrogen which will be coupled with P-gp or the linker. For radiotracer development, all three have an anilino methyl group that can be radiolabeled with $^{11}$C-methyl triflate.

In a particular embodiment, the disclosure provides for multi-targeting agents for Aβ plaque removal in an Alzheimer's disease brain comprising an Aβ plaque targeting agent that is linked to a second Aβ plaque removal targeting agent that is a P-gp substrate, inhibitor, or inducer; or a nicotinic α4β2 receptor ligand. In another embodiment, the Aβ plaque targeting removal agent is a substrate, inhibitor or inducer for p-glycoprotein (P-gp). Examples of such P-gp substrates, include but are not limited to, colchicine, ciclosporin, dabigatran, digoxin, diltiazem, fexofenadine, indinavir, morphine, and sirolimus. Examples of P-gp inhibitors include, but are not limited to, amiodarone, clarithromycin, ciclosporin, colchicine, diltiazem, erythromycin, felodipine, ketoconazole, lansoprazole, omeprazole, nifedipine, paroxetine, reserpine, saquinavir, sertraline, quinidine, tamoxifen, verapamil, duloxetine, elacridar, CP 100356, aosuquidar, tariquidar, valspodar and reversan. Examples of P-gp inducers include, but are not limited to, carbamazepine, dexamethasone, doxorubicin, nefazodone, phenobarbital, phenytoin, prazosin, rifampicin, St. John's wort, tenofovir, tipranavir, trazodone, and vinblastine. In a particular embodiment, the multi-targeting agents disclosed herein comprise a P-gp substrate, such as fexofenadine, and verapamil (e.g., see FIG. 16). Verapamil is a well-studied P-gp substrate in PET studies. Demethylated verapamil, containing a phenolic hydroxyl will be used to derivatize and couple with the Aβ ligands (e.g., see FIG. 14). Derivatization of verapamil on this ring may be tolerated since it has been shown that absence of this ring still renders the remainder of the molecule as a P-gp substrate.

In a certain embodiment, the disclosure provides for multi-targeting agents for Aβ plaque removal in an Alzheimer's disease brain comprising an Aβ plaque targeting agent that is linked to a P-gp substrate having the structure of Formula II:

or pharmaceutically acceptable salt, solvate, or prodrug thereof, wherein,

Y is selected from:

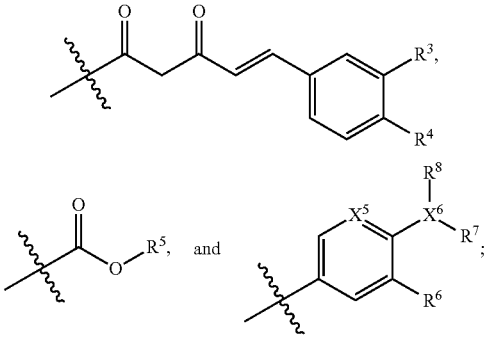

$X^1$, $X^2$, $X^5$ and $X^6$ are each independently selected from N and C;

$X^3$ is selected from H, O, S, N, NH, CH, and $CH_2$;

$X^4$ is selected from —O—, and —NR$^9$—;

n is an integer selected from 0, 1, 2, or 3;

$R^1$, $R^3$, and $R^4$ are each independently selected from H, —OH, and —OCH$_3$;

$R^2$, $R^5$, $R^7$ and $R^8$ are each independently selected from H, halo, hydroxyl, a $(C_1\text{-}C_3)$alkyl, and a —C(O)—$(C_1\text{-}C_3)$ alkyl, wherein the $(C_1\text{-}C_3)$alkyl, and the —C(O)—$(C_1\text{-}C_3)$ alkyl may further comprise one or more substitutions selected from halo, hydroxyl, amine, and a $(C_1\text{-}C_3)$alkoxy; and $R^6$ is H or a halo;

$R^9$ is an H or a $(C_1\text{-}C_3)$alkyl;

L is a linker as described herein; and m is an integer selected from 0 and 1.

In another embodiment, the disclosure provides for multi-targeting agents for Aβ plaque removal in an Alzheimer's disease brain comprising an Aβ plaque targeting agent that is linked to a P-gp substrate having the structure of Formula III:

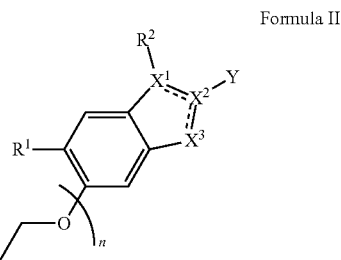

Formula II

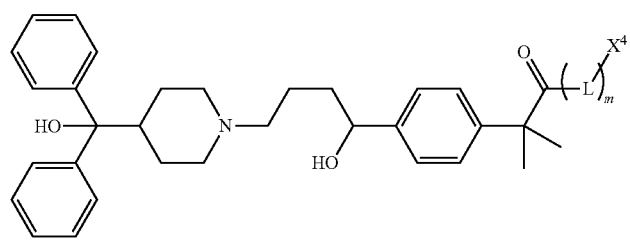

Formula III

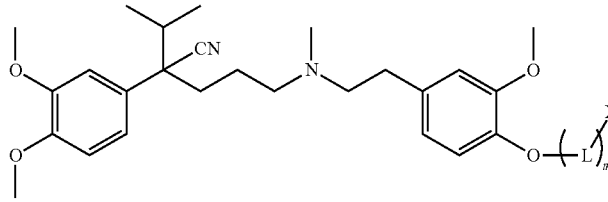

or pharmaceutically acceptable salt, solvate, or prodrug thereof, wherein,

Y is selected from:

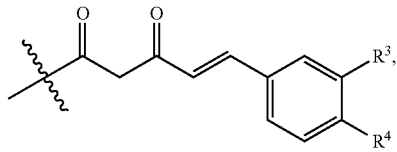

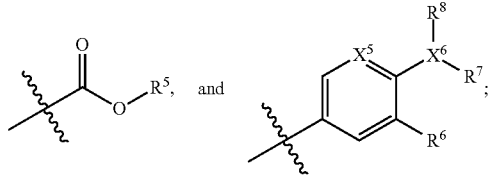

X$^1$, X$^2$, X$^5$ and X$^6$ are each independently selected from N and C;

X$^3$ is selected from H, O, S, N, NH, CH, and CH$_2$;

X$^4$ is selected from —O—, and —NR$^9$—;

n is an integer selected from 0, 1, 2, or 3;

R$^1$, R$^3$, and R$^4$ are each independently selected from H, —OH, and —OCH$_3$;

R$^2$, R$^5$, R$^7$ and R$^8$ are each independently selected from H, halo, hydroxyl, a (C$_1$-C$_3$)alkyl, and a —C(O)—(C$_1$-C$_3$)alkyl, wherein the (C$_1$-C$_3$)alkyl, and the —C(O)—(C$_1$-C$_3$)alkyl may further comprise one or more substitutions selected from halo, hydroxyl, amine, and a (C$_1$-C$_3$)alkoxy; and R$^6$ is H or a halo;

R$^9$ is an H or a (C$_1$-C$_3$)alkyl;

L is a linker as described herein; and m is an integer selected from 0 and 1.

Figure 15:
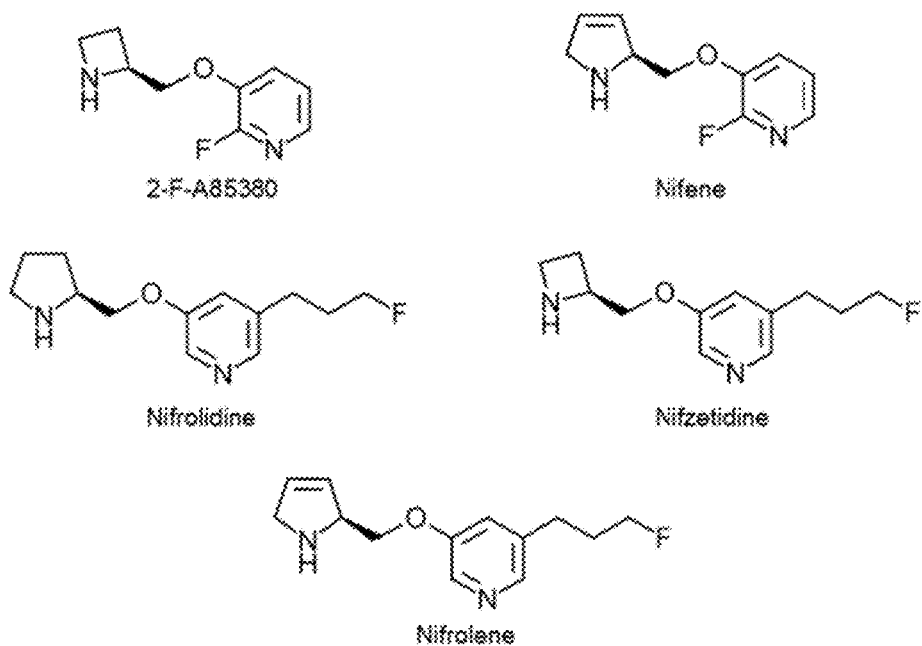
FIG. 15 presents embodiments of nicotinic α4β2 receptor targeting ligands that can be used to produce additional Aβ multi-targeting agents of the disclosure. Structure of nicotinic a4b2 receptor ligands that may be incorporated into the multi-agents. These include 2-F-A85380, Nifene, Nifzetidine and Nifrolene.

In an alternate embodiment, the multi-targeting agents disclosed herein comprise a ligand for the nicotinic α4β2 receptor. Examples of ligands for the nicotinic α4β2 receptors, include but are not limited to, 5-I-A85380, Nifene, Nifzetidine Nifrolidine, Nifrolene, Niodene, Niofene, Venlafaxine, ASEM (e.g., see FIG. 15).

In a certain embodiment, the disclosure provides for multi-targeting agents for Aβ plaque removal in an Alzheimer's disease brain comprising an Aβ plaque targeting agent that is linked to a ligand for the nicotinic α4β2 receptor having the structure of Formula IV:

Formula IV

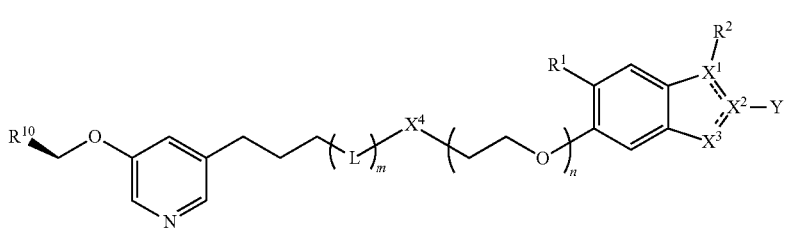

or pharmaceutically acceptable salt, solvate, or prodrug thereof, wherein,

Y is selected from:

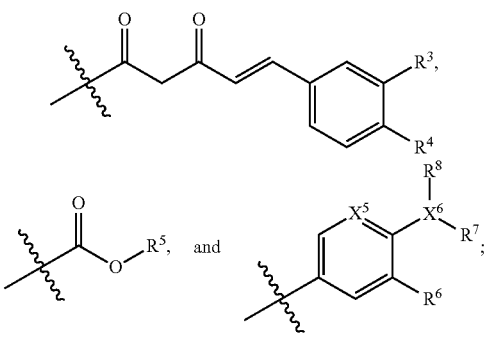

X$^1$, X$^2$, X$^5$ and X$^6$ are each independently selected from N and C;

X$^3$ is selected from H, O, S, N, NH, CH, and CH$_2$;

X$^4$ is selected from —O—, and —NR$^9$—;

n is an integer selected from 0, 1, 2, or 3;

$R^1$, $R^3$, and $R^4$ are each independently selected from H, —OH, and —OCH$_3$;

$R^2$, $R^5$, $R^7$ and $R^8$ are each independently selected from H, halo, hydroxyl, a (C$_1$-C$_3$)alkyl, and a —C(O)—(C$_1$-C$_3$)alkyl, wherein the (C$_1$-C$_3$)alkyl, and the —C(O)—(C$_1$-C$_3$)alkyl may further comprise one or more substitutions selected from halo, hydroxyl, amine, and a (C$_1$-C$_3$)alkoxy; and $R^6$ is H or a halo;
$R^9$ is an H or a (C$_1$-C$_3$)alkyl;
$R^{10}$ is

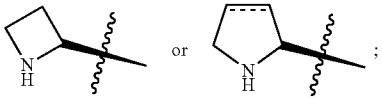

L is a linker as described herein; and
m is an integer selected from 0 and 1.

In another embodiment, the disclosure provides for multi-targeting agents for Aβ plaque removal in an Alzheimer's disease brain comprising an Aβ plaque targeting agent that is linked to a ligand for the nicotinic α4β2 receptor having the structure of Formula V:

Formula V

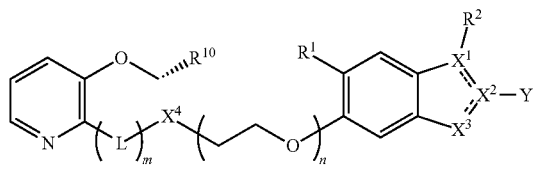

or pharmaceutically acceptable salt, solvate, or prodrug thereof, wherein,
Y is selected from:

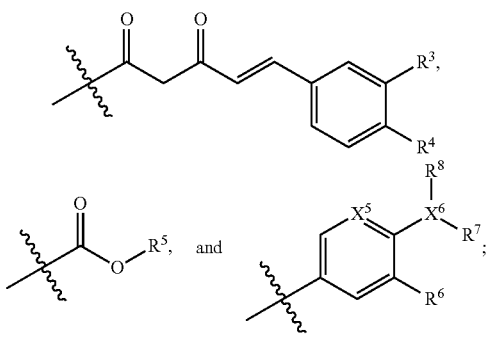

$X^1$, $X^2$, $X^5$ and $X^6$ are each independently selected from N and C;
$X^3$ is selected from H, O, S, N, NH, CH, and CH$_2$;
$X^4$ is selected from —O—, and —NR$^9$—;
n is an integer selected from 0, 1, 2, or 3;
$R^1$, $R^3$, and $R^4$ are each independently selected from H, —OH, and —OCH$_3$;
$R^2$, $R^5$, $R^7$ and $R^8$ are each independently selected from H, halo, hydroxyl, a (C$_1$-C$_3$)alkyl, and a —C(O)—(C$_1$-C$_3$)alkyl, wherein the (C$_1$-C$_3$)alkyl, and the —C(O)—(C$_1$-C$_3$)alkyl may further comprise one or more substitutions selected from halo, hydroxyl, amine, and a (C$_1$-C$_3$)alkoxy; and $R^6$ is H or a halo;
$R^9$ is an H or a (C$_1$-C$_3$)alkyl;
$R^{10}$ is

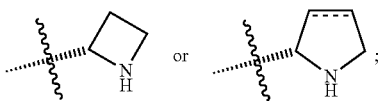

L is a linker as described herein; and
m is an integer selected from 0 and 1.

The disclosure provides that the multi-targeting agents of the disclosure may further comprise a linker which connects Aβ plaque targeting agent with the Aβ plaque removal targeting agent. The synthesis of the multi-targeting agents with a linker generally can be accomplished in little as two steps. In a particular embodiment, the linker comprises terminal functional group(s) (e.g., halides, tosylates, amines, hydroxyls, etc.) that are used to couple the linker to the Aβ plaque targeting agent and to the Aβ plaque removal targeting agent, thereby linking the two targeting regions together. Examples of such linkers include linker based on diglycolamine, triglycolamine, ethylene glycol, diethylene glycol, FG$^1$ (CH$_2$CH$_2$O)$_n$(CH$_2$)$_2$FG$^2$, and FG$^1$ (CH$_2$)$_n$FG$^2$, wherein FG$^1$ and FG$^2$ are each individually selected from Br, I, Cl, —OH, —NH, —SH, tosyl, mesyl, organolithium, sulfonyl, and wherein n is an integer selected from 1, 2, 3, 4, 5, 6, 7, 8, 9, 10, or a range that includes or is between any two of the foregoing integers, preferably wherein FG$^1$ and FG$^2$ are not the same functional group. example of synthesis protocols using such linkers to make multi-targeting agents of the disclosure includes as follows: in the first step the carboxylic acid group in fexofenadine is coupled to the amino group of glycolamine to form an amide using BOP; this intermediate, fexofenadine-glycolamide is coupled to N-BOC protected PIB, N-BOC protected AV-45 (fluorine replaced with a hydroxyl) and DAZA using the DIAD/Ph$_3$P method to connect the two with an ether linkage (in the case of PIB and AV-45) or with an amino-oxy linkage in the case of DAZA. Another example of synthesis protocols using such linkers to make multi-targeting agents of the disclosure includes as follows: polyethylene glycol (PEG$_2$ and PEG$_3$), is reacted in the presence of DIAD/PH$_3$P to provide verapamil-PEG; verapamil-PEG is be coupled to N-BOC protected PIB, N-BOC protected AV-45 (fluorine replaced with a hydroxyl) and DAZA using the DIAD/Ph$_3$P method to connect the two with an ether linkage (in the case of PIB and AV-45) or with an amino-oxy linkage in the case of DAZA.

In a particular embodiment, the disclosure provides for multi-targeting agent which has a structure selected from:

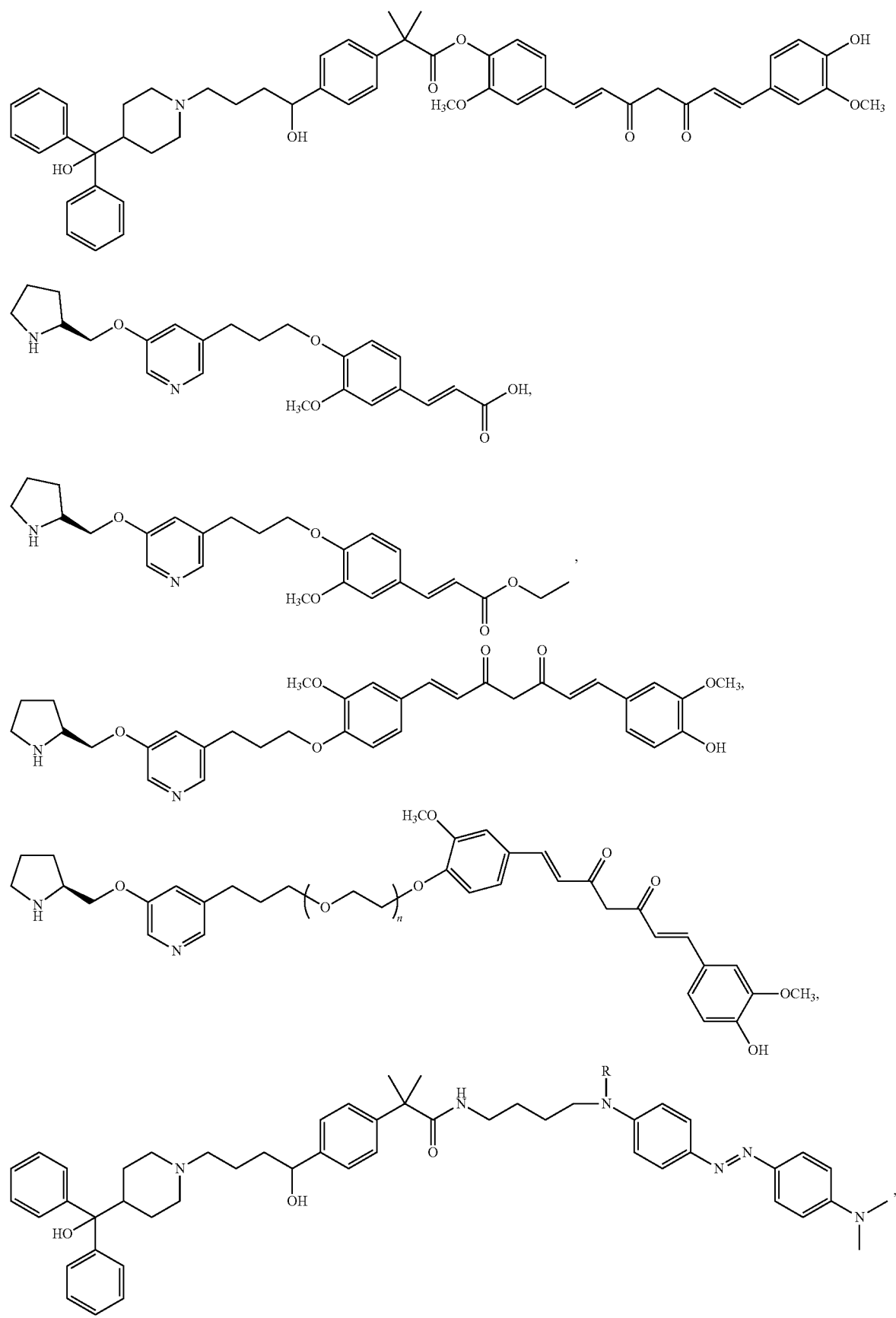

-continued

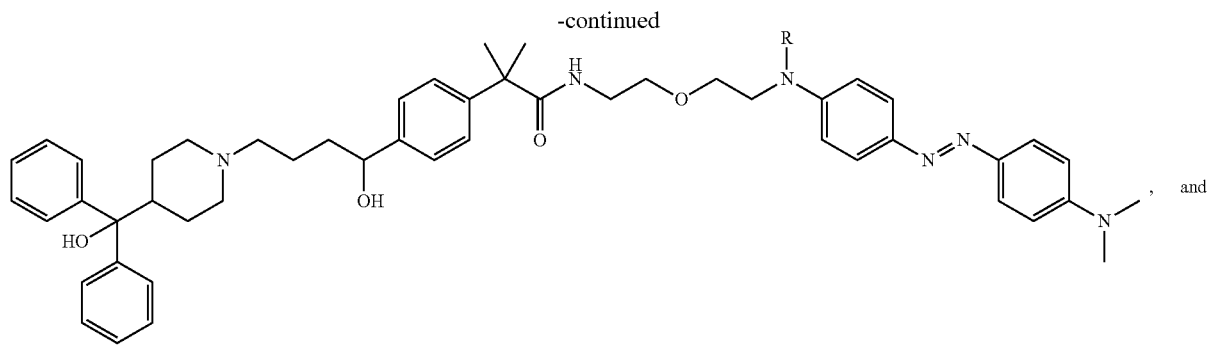

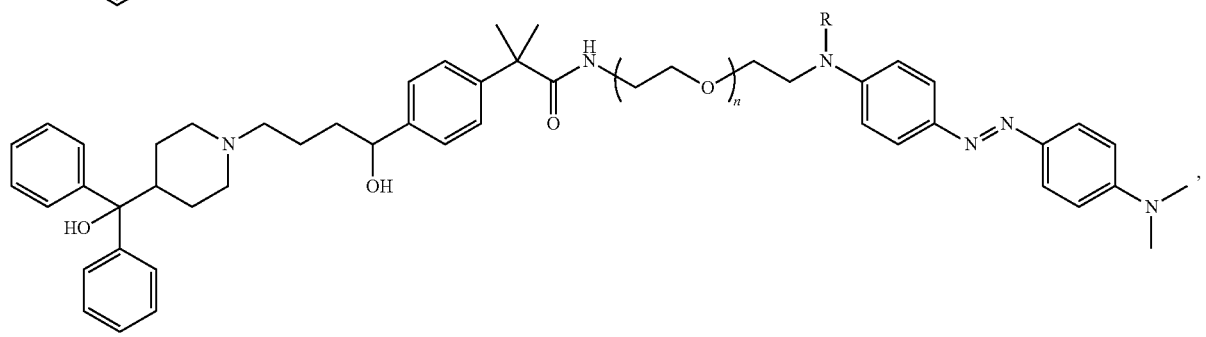

or a pharmaceutically acceptable salt, solvate, or prodrug thereof, wherein R is H or —CH$_3$; and n is an integer from 1 to 10.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The multi-targeting agent may also be provided as a prodrug, which is a functional derivative of the multi-targeting agent and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325;

Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

The multi-targeting agents disclosed herein may further comprise additional targeting ligands, like ligands which target the multi-targeting agents to the brain. Examples of such ligands, include peptides derived from rabies viral glycoprotein (RVG) (e.g., see Cui et al., *Immunity & Aging* 16:10 (2019), the disclosure of which is incorporated herein in its entirety).

The disclosure further provides for a pharmaceutical composition comprising the multi-targeting agents of the disclosure. Such pharmaceutical compositions may comprise physiologically acceptable surface-active agents, carriers, diluents, excipients, smoothing agents, suspension agents, film forming substances, and coating assistants, or combinations thereof. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

Techniques for formulation and administration of the compositions described herein may be found in "Remington's Pharmaceutical Sciences," Mack Publishing Co., Easton, Pa., 18th edition, 1990.

Suitable routes of administration of the pharmaceutical composition may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The pharmaceutical composition can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the disclosure may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the multi-targeting agents in water-soluble form. Additionally, suspensions of the multi-targeting agents may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the multi-targeting agents to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the multi-targeting agents can be formulated readily by combining the multi-targeting agents with pharmaceutically acceptable carriers well known in the art. Such carriers enable the multi-targeting agents of the disclosure to be formulated as tablets, pills, dragees, capsules, liquids, gels, syrups, slurries, suspensions and the like, for oral ingestion by a patient to be treated. Pharmaceutical preparations for oral use can be obtained by combining the multi-targeting agents with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active multi-targeting agent doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the multi-targeting agents may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the multi-targeting agents for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insulator may be formulated containing a powder mix of the compound and a suitable powder base such as lactose or starch.

Further disclosed herein are various pharmaceutical compositions well known in the pharmaceutical art for uses that include intraocular, intranasal, and intra-auricular delivery. Suitable penetrants for these uses are generally known in the art. Pharmaceutical compositions for intraocular delivery include aqueous ophthalmic solutions of the multi-targeting agents in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocil. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intra-auricular delivery include suspensions and ointments for topical application in the ear. Common solvents for such aural formulations include glycerin and water.

The pharmaceutical composition may also be formulated in rectal compositions such as suppositories or retention enemas, e.g., containing conventional suppository bases such as cocoa butter or other glycerides.

In addition to the pharmaceutical formulations described previously, the multi-targeting agents may also be formulated as a depot preparation. Such long acting formulations may be administered by implantation (for example subcutaneously or intramuscularly) or by intramuscular injection. Thus, for example, the multi-targeting agents may be formulated with suitable polymeric or hydrophobic materials (for example as an emulsion in an acceptable oil) or ion exchange resins, or as sparingly soluble derivatives, for example, as a sparingly soluble salt.

For hydrophobic multi-targeting agents, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethyl sulfoxide also may be employed, although usually at the cost of greater toxicity. Additionally, the multi-targeting agents may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the multi-targeting agents for a few weeks up to over 100 days. Depending on the chemical nature and the biological stability of the therapeutic reagent, additional strategies for protein stabilization may be employed.

Multi-targeting agents intended to be administered intracellularly may be administered using techniques well known to those of ordinary skill in the art. For example, the multi-targeting agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

The disclosure further provides methods of treatment using the multi-targeting agents of the disclosure. In particular, the multi-targeting agents of the disclosure can be used to treat a subject with Alzheimer's disease (and possibly Parkinson's disease). As shown in the studies presented herein, the multi-targeting agents of the disclosure can provide for the removal of Aβ plaques from diseased brain tissue and surrounding vasculature. The disclosure further provides that the multi-targeting agents can be co-administered with other known Alzheimer's disease treatment therapies, such as acetylcholinesterase inhibitors (AChEI) and memantine.

The following examples are intended to illustrate but not limit the disclosure. While they are typical of those that might be used, other procedures known to those skilled in the art may alternatively be used.

EXAMPLES

General Methods. All chemicals and solvents were of analytical or HPLC grade from Aldrich Chemical Co. and Fisher Scientific. Electrospray mass spectra were obtained on a Model 7250 mass spectrometer (Micromass LCT). Proton NMR spectra were recorded on a Bruker OMEGA 600 MHz spectrometer. Analytical thin layer chromatography (TLC) was carried out on silica coated plates (Baker-Flex, Phillipsburg, N.J.). Chromatographic separations were carried out on preparative TLC (silica gel GF 20×20 cm 2000 micron thick; Alltech Assoc. Inc., Deerfield, Ill.) or silica gel flash columns or semi-preparative reverse-phase columns using the Gilson high performance liquid chromatography (HPLC) systems. Rat and human postmortem brain slices were obtained on a Leica 1850 cryotome. [$^3$H]Cytisine and [$^3$H]PIB autoradiographic studies were carried out by exposing tissue samples on storage phosphor screens. The apposed phosphor screens were read and analyzed by OptiQuant acquisition and analysis program of the Cyclone Storage Phosphor System (Packard Instruments Co., Boston, Mass.). All rodent studies were approved by the Institutional Animal Care and Use Committee (IACUC) of University of California, Irvine. All human postmortem brain tissue studies were approved by the Institutional Biosafety Committee (IBC) of University of California, Irvine.

Synthesis: Ethyl 3-methoxy-4-(1'-N-BOC-aminobutyryloxy)cinnamate 6: Ethyl ferulate 1 (45 mg; 0.2 mmol) was dissolved in tetrahydrofuran (1 mL). To this solution, potassium tert-butoxide (50 mg) was added at room temperature and stirred for 15 mins followed by the addition of N-BOC-4-bromobutan-1-amine (51 mg; 0.2 mmol) was added. The solution turned bright yellow and was stirred at room temperature for 24 hours. The reaction was then washed with saturated sodium bicarbonate and extracted with dichloromethane. The organic extract was purified on preparative silica gel TLC using 9:1 dichloromethane-methanol to provide 37 mg (~45% yield) of pure 6. Mass spectra (m/z, %): 394 ([M+H]$^+$, 10%), 416 ([M+Na]$^+$, 25%), 809 ([2M+Na]$^+$, 100%). $^1$H NMR (CDCl$_3$, 600 MHz) δ ppm: 7.54 (d, 2H, J=15.9 Hz), 7.05 (d, 1H, J=8.2 Hz), 6.77 (d, 1H, J=8.2 Hz), 6.23 (d, 1H, J=15.9 Hz), 4.19 (m, 2H, OCH$_2$), 3.97 (m, 2H), 3.82 (s, 3H, OCH$_3$), 3.12 (m, 2H), 1.82 (m, 2H), 1.62 (m, 2H), 1.37 (s, 9H, N-BOC), 1.28 (t, 3H, CH$_3$).

Ethyl 3-methoxy-4-(1'-aminobutyryloxy)cinnamate 7: The N-BOC derivative 6 (20 mg; 50 μmol) was taken in dichloromethane (2 mL) into which 0.1 mL of trifluoroacetic acid was added. The reaction was stirred at ambient temperature for 24 hours. The reaction was quenched with saturated sodium bicarbonate and extracted with dichloromethane. The organic extract was purified on preparative silica gel TLC using 9:1 dichloromethane-methanol to provide 14 mg (~95% yield) of pure 7. Mass spectra (m/z, %): 294 (100%, [M+H]$^+$). 1H NMR (CDCl$_3$, 600 MHz) δ ppm: 7.62 (d, 2H, J=15.9 Hz), 7.08 (d, 1H, J=8.2 Hz), 6.84 (d, 1H, J=8.2 Hz), 6.31 (d, 1H, J=15.9 Hz), 4.26 (m, 2H, OCH$_2$), 4.09 (br, 2H), 3.82 (s, 3H, OCH3), 3.11 (br, 2H), 1.90-2.05 (br, 4H), 1.34 (t, 3H, CH3).

Fexofenadine-(3-methoxy-4-(1'-aminobutyryloxy)cinnamic acid 8: Fexofenadine 4 (13 mg; 26 μmol) was dissolved in acetonitrile (2 mL). To this solution, amine 7 (10 mg; 34 μmol) was added followed by addition of BOP (15 mg; 34 μmol) along with 0.1 mL triethylamine. The mixture was stirred at ambient temperature for 24 hours. The reaction solvent was removed and the residue was taken up in dichloromethane and washed with saturated sodium bicarbonate. The organic layer was dried and purified on preparative silica gel TLC using 9:1 dichloromethane-methanol to provide 11 mg (~54% yield) of pure amide in >95%. Mass spectra (m/z, %): 777 ([M+H]+, 55%). This amide was taken in methanol (0.5 mL) into which 0.5 mL of 1N sodium hydroxide was added. The reaction mixture was heated at 60° C. for 30 mins. The reaction was quenched with water and extracted with dichloromethane. The organic extract was purified on preparative silica gel TLC using 1:1 dichloromethane-methanol to provide pure 8. Mass spectra (m/z, %): 749 ([M+H]$^+$, 20%). 1H NMR (CDCl$_3$, 600 MHz) δ ppm: 7.62 (d, 2H, J=15.9 Hz), 7.50 (m, 4H), 7.28-7.35 (br, 8H), 7.20-7.13 (m, 2H), 6.84 (d, 1H, J=8.2 Hz), 6.36 (d, 1H, J=15.9 Hz), 4.09 (br, 2H), 3.82 (s, 3H, OCH$_3$), 3.50 (m, 2H), 3.11 (br, 2H), 3.01 (m, 3H), 2.93 (m, 2H), 1.90-2.05 (br, 4H), 1.72 (br, 8H), 1.52 (6H, m).

Fexofenadine curcuminate 9: Fexofenadine 4 (26.9 mg; 54 μmol) was dissolved in acetonitrile (2 mL). To this solution, curcumin 3 (18.6 mg; 50 μmol) was added followed by addition of BOP (23 mg; 52 µmol) along with 0.1 mL triethylamine. The solution turned bright orange and was stirred at room temperature for 24 hours. The reaction solvent was removed and the residue was taken up in dichloromethane and washed with saturated sodium bicarbonate. The organic layer was dried and purified on preparative silica gel TLC using 9:1 dichloromethane-methanol to provide 9 in >90% purity with an approximate yield of 25%. Mass spectra (m/z, %): 875 ([M+Na]$^+$, 30%). NMR (CDCl$_3$, 600 MHz) δ 7.62 (2H, m), 7.50 (2H, m), 7.33-7.39 (14H, m), 7.23 (2H, m), 7.11 (2H, m), 6.51 (2H, d, J=15.7 Hz), 5.24 (1H, s), 4.64 (1H, d,), 3.81 (3H, s), 3.79 (3H, s), 3.50 (2H, m), 3.01 (3H, m), 2.93 (2H, m), 1.63-1.77 (14H, m).

5-(3'-Ethyl 3-methoxy-4-propyloxycinnamate)-3-(1-BOC-2-(S)-pyrrolidinylmethoxy)pyridine 11: 5-(3-Tosyloxypropyl)-3-(1-BOC-2-(S)-pyrrolidinylmethoxy)pyridine 10 (34 mg, 70 µmol; prepared previously (Chattopadhyay et al., 2005) was reacted with ethyl ferulate 1 (20 mg, 90 µmol) in dimethylformamide (1 mL) in the presence of potassium tert-butoxide (12 mg). The reaction was heated for 24 hours at 100° C. and subsequently water (2 mL) was added and the mixture was extracted with dichloromethane. The dichloromethane extract was purified on preparative silica gel TLC using 9:1 dichloromethane-methanol to provide 11 in >95% purity and a yield of approx. 30%. Mass spectra (m/z, %), 541 ([M+H]$^+$, 100%), 563 ([M+Na]$^+$, 90%). NMR (CDCl$_3$, 600 MHz) δ ppm: 8.10 (s, 1H), 8.04 (s, 1H), 7.62 (d, 2H, J=15.9 Hz), 7.60 (s, 1H), 7.07 (d, 1H, J=8.2 Hz), 7.04 (s, 1H), 6.92 (d, 1H, J=8.2 Hz), 6.30 (d, 2H, J=15.9 Hz), 4.26 (m, 2H, OCH$_2$), 4.11 (m, 2H), 3.95 (m, 1H), 3.65 (m, 2H), 3.39 (m, 2H), 3.93 (s, 3H, OCH$_3$), 2.78 (m, 2H), 1.99 (m, 6H), 1.47 (s, 9H, N-BOC), 1.27 (s, 3H, CH$_3$).

5-(3'-Ethyl 3-methoxy-4-propyloxycinnamate)-3-(2-(S)-pyrrolidinylmethoxy)pyridine 12: The substituted ethyl ferulate 11 (5 mg; 9 µmol) was taken in dichloromethane (1 mL) into which 0.1 mL of trifluoroacetic acid was added. The reaction was stirred at ambient temperature for 24 hours. The reaction was quenched with saturated sodium bicarbonate and extracted with dichloromethane. The organic extract was purified on preparative silica gel TLC using 9:1 dichloromethane-methanol to provide pure 12. Mass spectra (m/z, %), 413 ([M+H]$^+$, 75%). NMR (CD$_3$OD, 600 MHz) δ ppm: 8.13 (s, 1H), 8.06 (s, 1H), 7.62 (d, 2H, J=15.9 Hz), 7.60 (s, 1H), 7.05 (d, 1H, J=8.2 Hz), 7.02 (s, 1H), 6.92 (d, 1H, J=8.2 Hz), 6.30 (d, 2H, J=15.9 Hz), 4.27 (m, 2H, OCH2), 4.15 (m, 2H), 3.95 (m, 1H), 3.91 (s, 3H, OCH$_3$), 3.65 (m, 2H), 3.39 (m, 2H), 2.78 (m, 2H), 1.99 (m, 6H), 1.27 (s, 3H, CH$_3$).

5-(3-methoxy-4-propyloxycinnamate)-3-(2-(S)-pyrrolidinylmethoxy)pyridine 13: Ether 12 (4 mg; 10 µmol) was taken in methanol (0.5 mL) into which 0.5 mL of 1N sodium hydroxide was added. The reaction mixture was heated at 60° C. for 30 mins. The reaction was quenched with water and extracted with dichloromethane. The organic extract was purified on preparative silica gel TLC using 1:1 dichloromethane-methanol to provide pure 13. Mass spectra (m/z, %), 441 ([M+H]$^+$, 100%). NMR (CD$_3$OD, 600 MHz) δ ppm: 8.17 (s, 1H), 8.06 (s, 1H), 7.62 (d, 2H, J=15.9 Hz), 7.60 (s, 1H), 7.07 (d, 1H, J=8.2 Hz), 7.04 (s, 1H), 6.92 (d, 1H, J=8.2 Hz), 6.30 (d, 2H, J=15.9 Hz), 4.15 (m, 2H), 3.93 (m, 1H), 3.91 (s, 3H, OCH$_3$), 3.70 (m, 2H), 3.42 (m, 2H), 2.78 (m, 2H), 1.99 (m, 6H).

Preparation of multi-targeting agents containing DAZA and fexofenadine. DAZA was modified with 3 different linkers, N-butylamine (DAZA-BuNH$_2$; see FIG. 7), N-PEGlethylamine (DAZA-PEG1NH$_2$; see FIG. 8) and N-PEG2ethylamine (DAZA-PEG2NH$_2$; see FIG. 9). The carboxylic acid group in fexofenadine was used to form an amide bond with the 3 DAZA derivatives. Thus, DAZA-BuNH-FEX was prepared by coupling DAZA-BuNH$_2$ with fexofenadine using benzotriazol-1-yloxytris(dimethylamino) phosphonium hexafluorophosphate (BOP) as the coupling agent. Mass spectra of DAZA-BuNH-FEX (see FIG. 7) is shown with a molecular ion peak [M+H]$^+$=795.5, consistent with its molecular weight of 794.5. DAZA-PEG1NH-FEX was prepared by coupling DAZA-PEG1NH$_2$ with fexofenadine using BOP. Mass spectra of DAZA-PEG1NH-FEX (see FIG. 8) is shown with a molecular ion peak [M+H]$^+$=811.5, consistent with its molecular weight of 810.5. DAZA-PEG2NH-FEX was prepared by coupling DAZA-PEG2NH$_2$ with fexofenadine using BOP. Mass spectra of DAZA-PEG2NH-FEX (see FIG. 9) is shown with a molecular ion peak [M+H]$^+$=855.5, consistent with its molecular weight of 854.5.

The carboxylic acid functional group in fexofenadine was used to prepare the 3 fexofenadineamide derivatives, DAZA-BuNH-FEX, DAZA-PEG1NH-FEX and DAZA-PEG2NH-FEX which are all analogs of the high affinity Aβ plaques binding agent TAZA. The 3 derivatives are expected to be stable in vivo. It is also expected that modification of the carboxylic acid end of fexofenadine may not have major detrimental effects on its interaction with P-glycoprotein as a substrate. The 3 derivatives have different levels of flexibility and offer the ability to optimize brain permeability and efficiency optimization in their ability to remove Aβ plaques from the brain. The linkers can be used with other Aβ plaque binding agents and P-glycoprotein substrates.

In Vitro Studies: Ex vivo rat brain slices were prepared at 10 µm thick using a Leica 1850 cryotome and used for [$^3$H]cytisine binding. Autoradiographic studies using [$^3$H] cytisine and drug (GKS-006 and GKS-007) concentrations were carried out by exposing tissue radiolabeled brain sections on storage phosphor screens (Perkin Elmer Multisensitive, Medium MS). The apposed phosphor screens were read and analyzed by OptiQuant acquisition and analysis program of the Cyclone Storage Phosphor System (Packard Instruments Co., Boston, Mass.). Region-of-interest of same size were drawn and analyzed on brain regions using OptiQuant software and binding of [$^3$H]cytisine measured in Digital Light Units/mm$^2$ (DLU/mm$^2$). Data was analyzed using following procedure: (a) the non-specific binding of [$^3$H]cytisine was subtracted for all samples; (b) the specific binding was normalized to 100% (no competitive ligand) and (c) the binding isotherms were fit to the Hill equation (KELL BioSoft software (v 6), Cambridge, U.K.).

Post-mortem human AD frontal cortex sections (10 µm thick; human brain tissue obtained from Banner Sun Health Research Institute, Sun City, Ariz.) were preincubated in 10% alcohol PBS buffer for 10 minutes. The brain sections were placed in a glass chamber and incubated with [$^3$H]PIB (2 µCi/cc) in 10% alcohol PBS buffer, pH 7.4 at 37° C. for 1 h. The slices were then washed with cold 10% alcohol PBS buffer (2×3 mins), cold deionized water 1 min, respectively. The brain sections were air dried, exposed overnight on a phosphor film, and then placed on the Phosphor Autoradiographic Imaging System/Cyclone Storage Phosphor System (Packard Instruments Co). Regions of interest (ROIs) were drawn on the slices and the extent of binding of [$^3$H]PIB was measured with DLU/mm$^2$ using the OptiQuant acquisition and analysis program (Packard Instruments Co).

Figure 4:
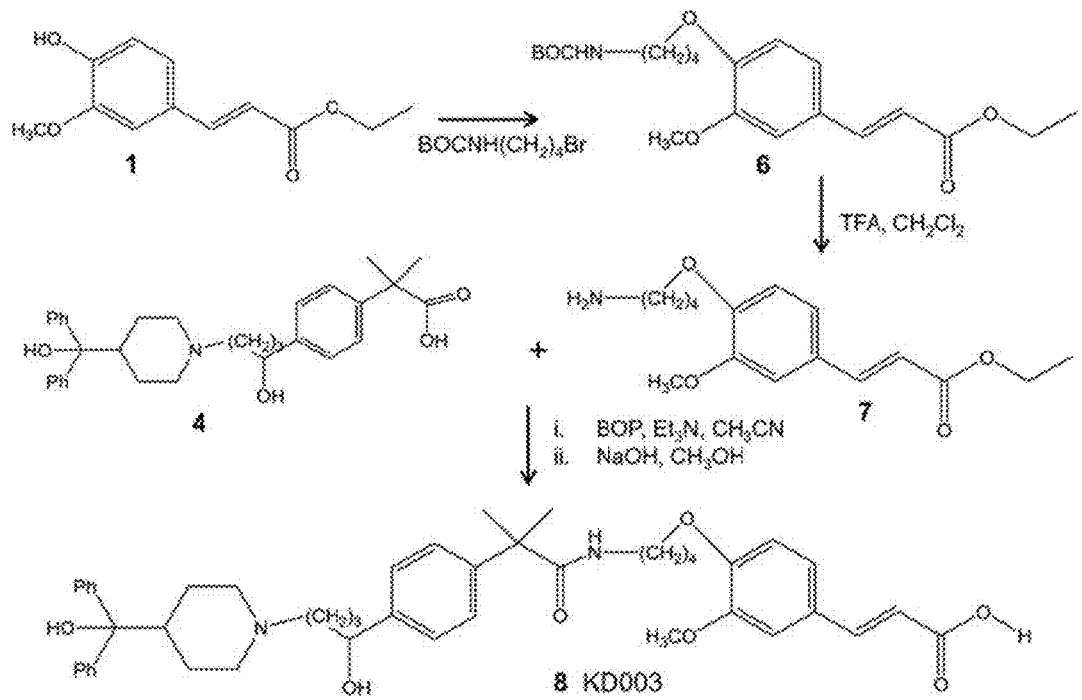
FIG. 4 presents the synthesis of Aβ-P-gp agents using linker. O-alkylation of FAEE 1 with N-BOC bromobutylamine to 6. Deprotection of N-BOC 6 with TFA, trifluoroacetic acid for 7. Amide formation with FEX 4 and 7 using BOP, benzotriazol-1-yloxy)tris(dimethylamino) phosphonium hexafluorophosphate followed by base hydrolysis to provide 8.

Results of synthesis: For P-gp and Aβ amyloid multi-agent, two different approaches were taken. FIG. 4 shows derivatization of FAEE with the 4-carbon linker. In the presence of base, the phenolate of FAEE 1 was reacted with N-BOC-1-bromo-4-butylamine to provide 6 in 45% yield. Removal of the N-BOC protecting group using trifluoroacetic acid resulted in the corresponding amine 7 in 95% yields. Fexofenadine 4 was coupled to the amine 7 using BOP to form the amide derivative of FAEE. Base hydrolysis of this amide-ester resulted in the FA derivative 8 in 50-60% yields.

Figure 5:
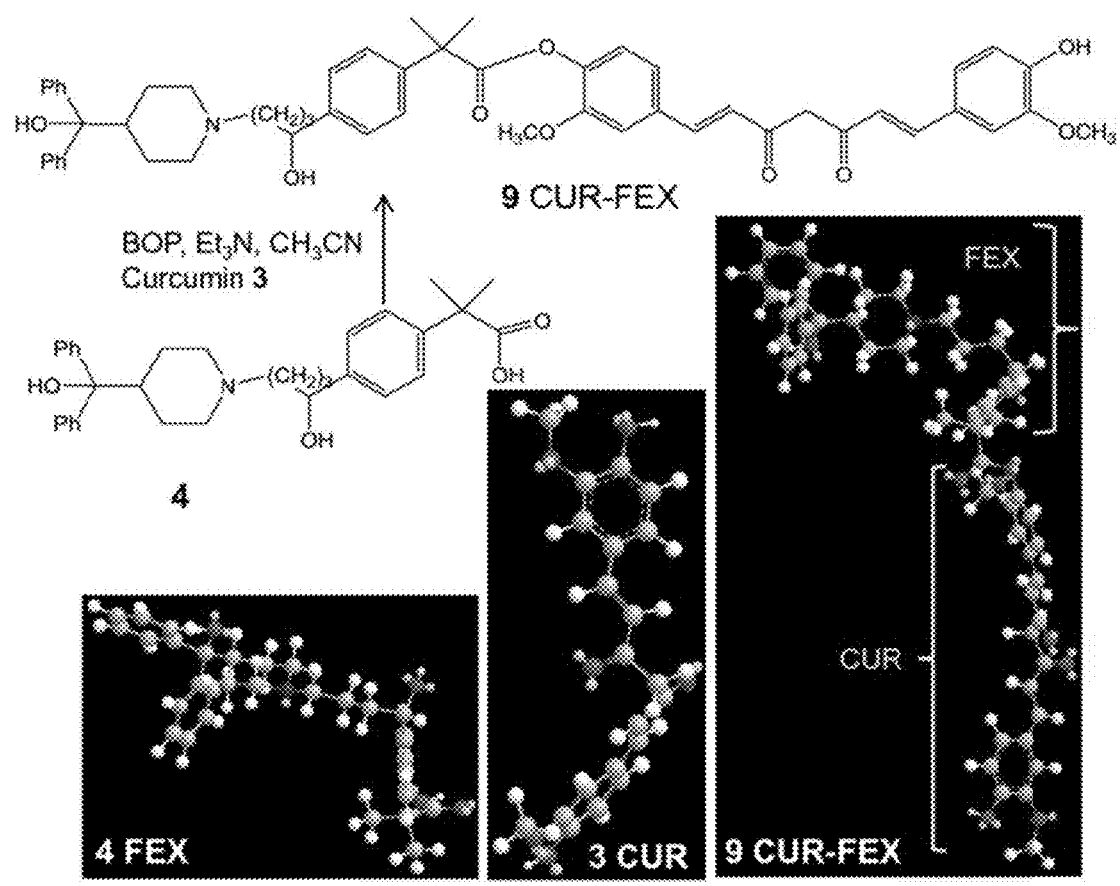
FIG. 5 provides for curcumin ester synthesis of Aβ-P-gp agent. Esterification of CUR 3 and FEX 4 using BOP. Energy-minimized models comparing the multi-agent, CURFEX 9 with CUR 3 and FEX 4.

The second approach for P-gp and Aβ amyloid multi-agent is shown in FIG. 5. Fexofenadine 4 was directly coupled to curcumin 3 using BOP to form the fexofenadine-curcumin derivative 9 in an ester linkage. This multi-agent ester was obtained in moderate yields. Potential steric effects from the adjacent gem-dimethyl group may have affected the yields. The use of the 4-carbon linker may help in increasing the coupling yield, with the formation of an ether-amide link between fexofenadine and curcumin.

To obtain multi-agent for α4β2* nAChRs and Aβ amyloid, the N-BOC tosylate 10 was used, which was synthesized previously. Coupling of the N-BOC tosylate 10 with ferulic acid ethyl ester (FAEE) 1 was carried out using nucleophilic substitution reaction by the phenolate of FAEE shown in FIG. 6. Ether 11 was obtained in 30% yields. Formation of the ether under Mitsunobu reaction conditions using DIAD/Ph₃P as the coupling agent did not provide good yields. Removal of the N-BOC protecting group using trifluoroacetic acid resulted in GKS-006 12 in 85-90% yield. Base hydrolysis of the ethyl ester in GKS-006 12 provided GKS-007 13 in 80% isolated yields. The purified GKS-006 and GKS-007 were used for in vitro studies.

Results of Aβ Plaque binding: The Aβ plaque-P-gp multi-agents, KD003 and CUR-FEX were tested for binding to Aβ amyloid plaques in human postmortem AD brain frontal cortex slices that were labeled with [³H]PIB (75-90 year olds, Braak score V-VI). FIG. 10A shows [³H]PIB labeling of human AD frontal cortex section which was greater in the gray matter (GM) regions compared to white matter (WM) regions with GM/WM ratio of approx. 3. In the presence of FA (10 μM) both GM and WM showed higher levels of [³H]PIB with a GM/WM ratio of 2 (e.g., see FIG. 10B). The multi-agent KD003 (e.g., see FIG. 10C, 10 μM) also showed higher levels of [³H]PIB with GM/WM ratio of 2.4. Curcumin (10 μM), known to have a high affinity for Aβ amyloid showed the lowest GM/WM ratio of 1.5 (e.g., see FIGS. 10E and G). The multi-agent of curcumin, CUR-FEX (10 μM) showed lower binding of [³H]PIB (e.g., see FIGS. 10D and F), with GM/WM ratio reduction to 1.96 as seen in FIG. 10G.

The Aβ plaque-α4β2* nAChR multi-agent was tested for binding to Aβ amyloid plaques in human postmortem AD brain frontal cortex slices labeled with [³H]PIB (75-90 year olds, Braak score V-VI). FIG. 11B shows [³H]PIB labeling of human AD frontal cortex section (e.g., see FIG. 11A) which was greater in the gray matter (GM) regions compared to white matter (WM) regions with GM/WM ratio of approx. 2. In the presence of TAZA (1 μM) which is known to bind to Aβ amyloid plaques with high affinity, significant displacement of [³H]PIB occurred from the GM regions (e.g., see FIG. 11C), with GM/WM ratio reducing to 1.3. Unlike the effects of TAZA, ferulic acid (FA, 1 μM) did not significantly affect the binding of [³H]PIB (e.g., see FIG. 11D), with GM/WM ratio of approx. 2 which was similar to that of the control (e.g., see FIG. 11B). Similarly the Aβ plaque-α4β2* nAChR multi-agent, GKS-007 10 (1 μM) containing FA appeared to have some inhibitory effect on [³H]PIB (e.g., see FIG. 11E), but there was no significant GM/WM ratio reduction as seen in FIG. 11G.

Nicotinic receptor binding: The Aβ plaque-α4β2* nAChR multi-agents were tested for their affinity to the α4β2* nAChRs using rat brain slices labeled with [³H] cytisine. FIG. 12 shows [³H]cytisine labeling of rat brain regions of thalamus, frontal cortex, striatum, subiculum and cerebellum. Displacement of significant amounts of [³H] cytisine was observed by 100 nM of GKS-006 (e.g., see FIG. 12C) and 100 nM GKS-007 (e.g., see FIG. 12D). Three brain regions analyzed included thalamus, frontal cortex and subiculum. With increasing concentration of GKS-006 (e.g., see FIGS. 12E and G) and GKS-007 (e.g., see FIGS. 12F and H) binding of [³H]cytisine was reduced from all brain regions. Measured inhibitory constants (IC₅₀) of GKS-006 in the various brain regions were: thalamus=2.80 nM; frontal cortex=5.33 nM; subiculum=2.83 nM. Similarly, measured inhibitory constants (IC₅₀) of GKS-007 in the various brain regions were: thalamus=3.44 nM; frontal cortex=3.18 nM; subiculum=5.40 nM.

It will be understood that various modifications may be made without departing from the spirit and scope of this disclosure. Accordingly, other embodiments are within the scope of the following claims.

What is claimed is:

1. A multi-targeting agent that assists in the targeted removal of amyloid beta plaques from a brain and surrounding vasculature, comprising:
   an amyloid beta (Aβ) plaque targeting agent that exhibits moderate to high binding affinity to Aβ plaques;
   an Aβ plaque targeting removal agent which assists or promotes removal of Aβ plaques from a brain and surrounding vasculature;
   wherein, the Aβ plaque targeting agent is indirectly linked to the Aβ plaque targeting removal agent via the use of a covalently attached linker, and
   wherein the Aβ plaque targeting agent comprises the structure of Formula (I):

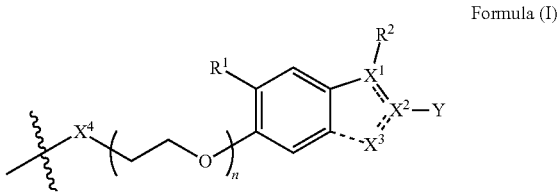

Formula (I)

or a pharmaceutical acceptable salt, solvate or prodrug thereof, wherein,
Y is:

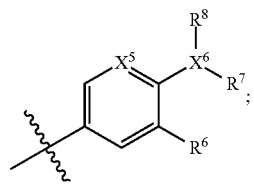

$X^1$, $X^2$, $X^5$ and $X^6$ are each independently selected from N and C;
$X^3$ is absent or selected from H, O, S, N, NH, CH, and $CH_2$;
$X^4$ is selected from —O—, and —NR⁹—;
n is an integer selected from 0, 1, 2, or 3;

$R^1$ is selected from H, —OH, and —OCH$_3$;

$R^2$, $R^7$ and $R^8$ are each independently selected from H, halo, hydroxyl, a (C$_1$-C$_3$)alkyl, and a —C(O)—(C$_1$-C$_3$) alkyl, wherein the (C$_1$-C$_3$)alkyl, and the —C(O)—(C$_1$-C$_3$)alkyl may further comprise one or more substitutions selected from halo, hydroxyl, amine, and a (C$_1$-C$_3$)alkoxy;

$R^6$ is H or a halo; and $R^9$ is an H or a (C$_1$-C$_3$)alkyl.

2. The multi-targeting agent of claim 1, wherein the Aβ plaque targeting agent comprises a structure selected from:

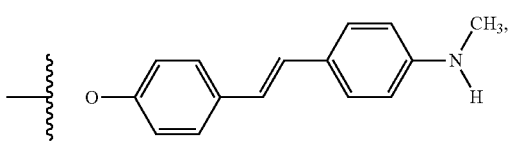

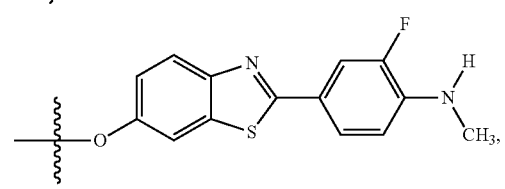

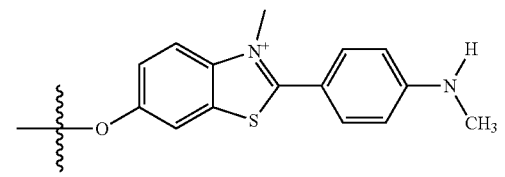

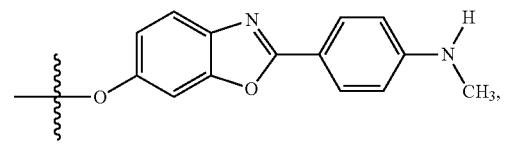

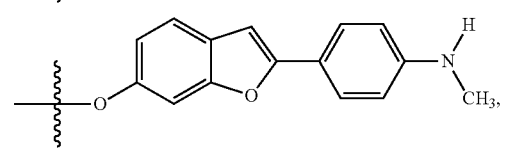

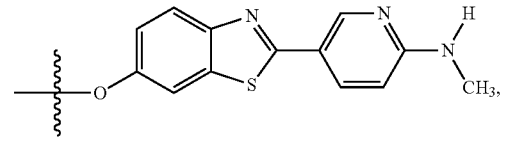

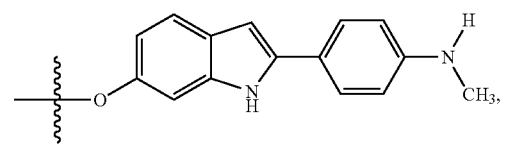

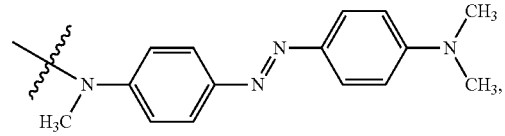

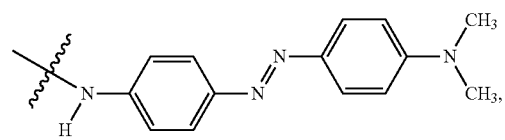

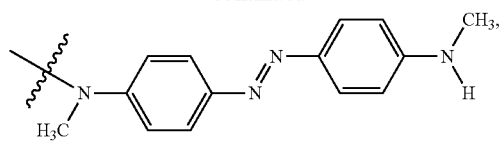

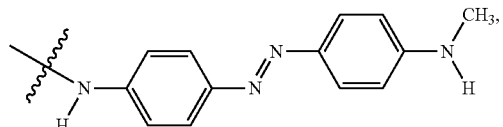

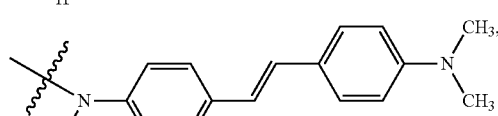

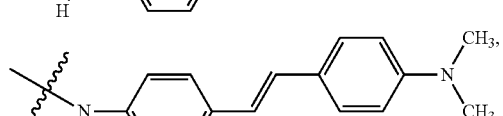

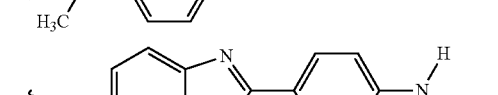, and

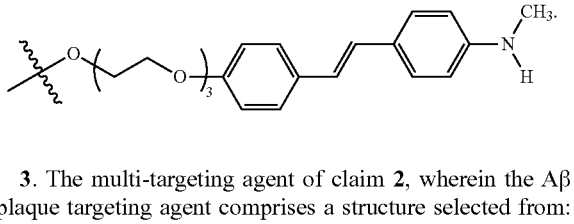

3. The multi-targeting agent of claim 2, wherein the Aβ plaque targeting agent comprises a structure selected from:

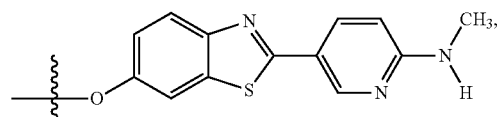

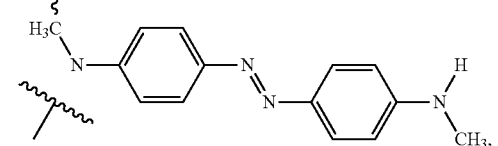

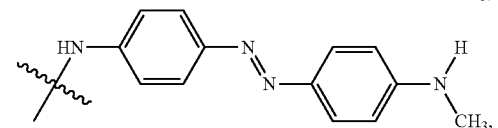

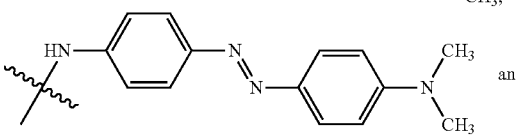 and

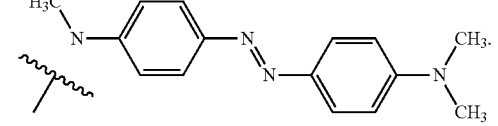

4. The multi-targeting agent of claim 3, wherein the Aβ plaque targeting agent comprises the structure of:

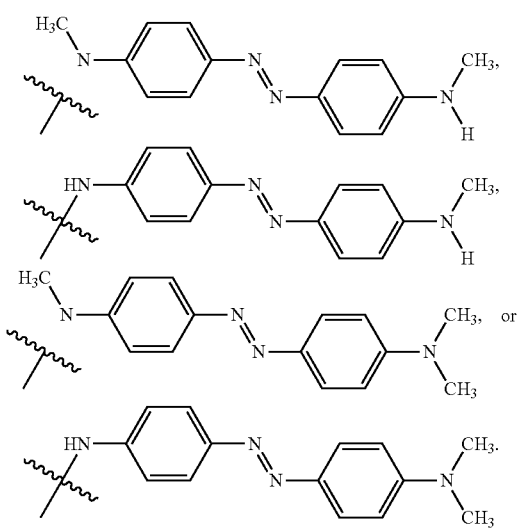

5. The multi-targeting agent of claim 1, wherein the Aβ plaque targeting removal agent is a substrate, inhibitor or inducer for p-glycoprotein (P-gp) selected from colchicine, ciclosporin, dabigatran, digoxin, diltiazem, fexofenadine, indinavir, morphine, sirolimus, amiodarone, clarithromycin, ciclosporin, colchicine, diltiazem, erythromycin, felodipine, ketoconazole, lansoprazole, omeprazole, nifedipine, paroxetine, reserpine, saquinavir, sertraline, quinidine, tamoxifen, verapamil, duloxetine, elacridar, CP 100356, aosuquidar, tariquidar, valspodar, reversan, carbamazepine, dexamethasone, doxorubicin, nefazodone, phenobarbital, phenytoin, prazosin, rifampicin, tenofovir, tipranavir, trazodone, and vinblastine, or a derivative of any of the foregoing.

6. The multi-targeting agent of claim 5, wherein the Aβ plaque targeting removal agent is fexofenadine, verapamil, or a derivative of any of the foregoing.

7. The multi-targeting agent of claim 1, wherein the Aβ plaque targeting removal agent is a ligand for nicotinic a4β2 receptors.

8. The multi-targeting agent of claim 7, wherein the Aβ plaque targeting removal agent is selected from 2-F-A85380, 5-I-A85380, Nifene, Nifzetidine Nifrolidine, Nifrolene, Niodene, Niofene, Venlafaxine, ASEM or a derivative of any of the foregoing.

9. The multi-targeting agent of claim 8, wherein the Aβ plaque targeting removal agent is Nifrolidine or a derivative thereof.

10. The multi-targeting agent of claim 1, wherein the Aβ plaque targeting agent is linked indirectly to the Aβ plaque targeting removal agent via the use of a covalently attached optionally substituted ($C_2$ to $C_{10}$)-alkyl linker, or an optionally substituted ($C_2$ to $C_{10}$)-alkoxy linker.

11. The multi-targeting agent of claim 10, wherein the ($C_2$ to $C_{10}$)alkyl linker or the ($C_2$ to $C_{10}$)-alkoxy linker comprises terminal functional groups that can undergo coupling reactions with the Aβ plaque targeting agent and with the Aβ plaque targeting removal agent.

12. The multi-targeting agent of claim 10, wherein the ($C_2$ to $C_{10}$)alkyl linker or the ($C_2$ to $C_{10}$)-alkoxy linker is selected from 1-amino-4-butanol, ethylene glycol, diethylene glycol, diglycolamine, —$(CH_2)_wO(CH_2)_xNH$—, —$(CH_2CH_2O)_yCH_2CH_2NH$—, —$(CH_2)_zNH$—, and triglycolamine, wherein w, x, y and z are each integers independently selected from 1, 2, 3, 4, 5, 6, 7, 8, 9, and 10.

13. The multi-targeting agent of claim 1, wherein the multi-targeting targeting agent has a structure selected from the group consisting of:

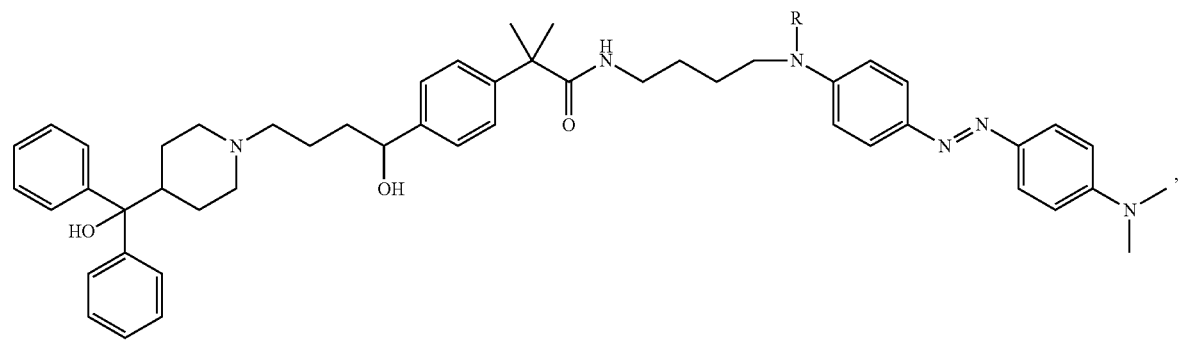

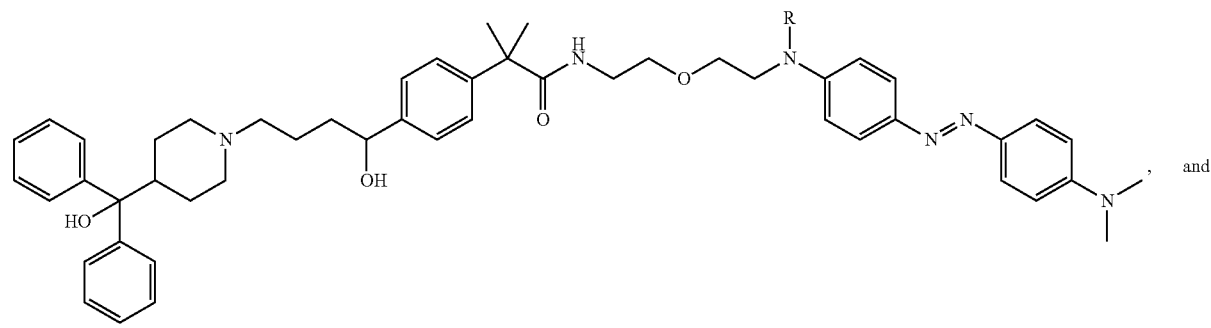

-continued

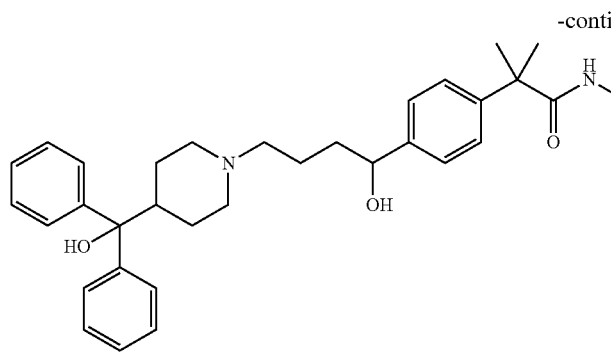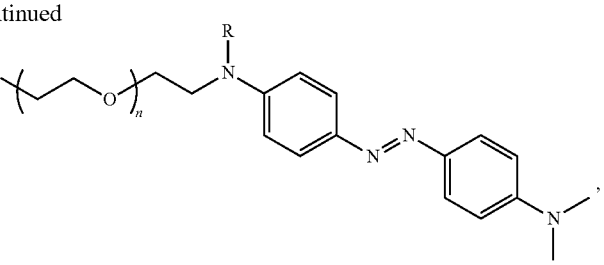

wherein, R is H or —CH$_3$; and n is an integer from 1 to 10.

14. A pharmaceutical composition comprising the multi-targeting agent of claim 1 and a pharmaceutically acceptable carrier.

15. The pharmaceutical composition of claim 14, wherein the pharmaceutical composition is formulated for oral or parenteral delivery.

16. A method of treating a subject with Alzheimer's disease, comprising:
administering a therapeutically effective amount of the pharmaceutical composition of claim 14 to the subject.

17. The method of claim 16, further comprising the step of:
administering concomitantly or sequentially to the subject effective amounts of one or more Alzheimer's treatments selected from the group consisting of cholinesterase inhibitors, antidepressants, anxiolytics, antipsychotic medications, tricyclic antidepressants, benzodiazepines, sleeping pills, atypical antipsychotics, memantine and haloperidol.

18. A method of clearing Aβ plaques from a subject with Alzheimer's disease comprising:
administering a therapeutically effective amount of the pharmaceutical composition of claim 14 to the subject.

19. The method of claim 18, further comprising:
administering concomitantly or sequentially to the subject effective amounts of one or more Alzheimer's treatments selected from the group consisting of cholinesterase inhibitors, antidepressants, anxiolytics, antipsychotic medications, tricyclic antidepressants, benzodiazepines, sleeping pills, atypical antipsychotics, memantine and haloperidol.

* * * * *